US009668972B2

(12) United States Patent
Tamarkin et al.

(10) Patent No.: US 9,668,972 B2
(45) Date of Patent: Jun. 6, 2017

(54) NONSTEROIDAL IMMUNOMODULATING KIT AND COMPOSITION AND USES THEREOF

(75) Inventors: Dov Tamarkin, Maccabim (IL); Meir Eini, Ness Ziona (IL); Doron Friedman, Karmei Yosef (IL)

(73) Assignee: FOAMIX PHARMACEUTICALS LTD., Rehovot (IL)

(*) Notice: Subject to any disclaimer, the term of this patent is extended or adjusted under 35 U.S.C. 154(b) by 1299 days.

(21) Appl. No.: 11/078,902

(22) Filed: Mar. 11, 2005

(65) Prior Publication Data

US 2005/0232869 A1   Oct. 20, 2005

Related U.S. Application Data

(63) Continuation-in-part of application No. 10/911,367, filed on Aug. 4, 2004, now abandoned, and a continuation-in-part of application No. PCT/IB03/05527, filed on Oct. 24, 2003.

(60) Provisional application No. 60/492,385, filed on Aug. 4, 2003, provisional application No. 60/429,546, filed on Nov. 29, 2002.

(30) Foreign Application Priority Data

Oct. 25, 2002 (IL) .......................................... 152486

(51) Int. Cl.
| | |
|---|---|
| *A61K 9/12* | (2006.01) |
| *A61K 8/04* | (2006.01) |
| *A61K 8/67* | (2006.01) |
| *A61K 31/07* | (2006.01) |
| *A61K 31/203* | (2006.01) |
| *A61Q 19/00* | (2006.01) |
| *A61K 9/00* | (2006.01) |
| *A61K 9/10* | (2006.01) |

(52) U.S. Cl.
CPC .............. *A61K 9/122* (2013.01); *A61K 8/046* (2013.01); *A61K 8/671* (2013.01); *A61K 9/0014* (2013.01); *A61K 31/07* (2013.01); *A61K 31/203* (2013.01); *A61Q 19/00* (2013.01); *A61K 9/10* (2013.01)

(58) Field of Classification Search
USPC .......................................................... 424/45
See application file for complete search history.

(56) References Cited

U.S. PATENT DOCUMENTS

| | | | |
|---|---|---|---|
| 1,159,250 A | 11/1915 | Moulton | |
| 1,666,684 A | 4/1928 | Carstens | |
| 1,924,972 A | 8/1933 | Beckert | |
| 2,085,733 A * | 7/1937 | Bird | ................ 424/73 |
| 2,390,921 A | 12/1945 | Clark | |
| 2,524,590 A | 10/1950 | Boe | |
| 2,586,287 A | 2/1952 | Apperson | |
| 2,617,754 A | 11/1952 | Neely | |
| 2,767,712 A | 10/1956 | Waterman | |
| 2,968,628 A * | 1/1961 | Reed | ................................ 516/7 |
| 3,004,894 A | 10/1961 | Johnson et al. | |
| 3,062,715 A | 11/1962 | Reese | |
| 3,067,784 A | 12/1962 | Gorman | |
| 3,092,255 A | 6/1963 | Hohman | |
| 3,141,821 A | 7/1964 | Compeau | |
| 3,142,420 A | 7/1964 | Gawthrop | |
| 3,144,386 A | 8/1964 | Brighttenback | |
| 3,149,543 A | 9/1964 | Naab | |
| 3,154,075 A | 10/1964 | Weckesser | |
| 3,178,352 A | 4/1965 | Erickson | |
| 3,236,457 A | 2/1966 | Kennedy et al. | |
| 3,244,589 A * | 4/1966 | Sunnen et al. | .................. 424/45 |
| 3,252,859 A | 5/1966 | Silver | |
| 3,261,695 A | 7/1966 | Sienciewicz | |
| 3,263,867 A | 8/1966 | Lehmann | |
| 3,263,869 A | 8/1966 | Corsette | |
| 3,298,919 A | 1/1967 | Charles et al. | |
| 3,301,444 A | 1/1967 | Wittke | |
| 3,303,970 A | 2/1967 | Breslau et al. | |
| 3,330,730 A | 7/1967 | Emil Hernaadez | |
| 3,333,333 A | 8/1967 | Noack | |
| 3,334,147 A | 8/1967 | Brunelle et al. | |
| 3,342,845 A | 9/1967 | Sayigh et al. | |
| 3,346,451 A | 10/1967 | Collins et al. | |
| 3,366,494 A | 1/1968 | Bower | |
| 3,369,034 A | 2/1968 | Chalmers | |
| 3,377,004 A | 4/1968 | Wittke | |
| 3,383,280 A | 5/1968 | Kuehns | |
| 3,384,541 A | 5/1968 | Clark et al. | |
| 3,395,214 A | 7/1968 | Mummert | |

(Continued)

FOREIGN PATENT DOCUMENTS

| | | |
|---|---|---|
| AU | 198780257 | 9/1986 |
| AU | 782515 | 12/2005 |

(Continued)

OTHER PUBLICATIONS

Gschnait. Arch Dermatol Res (1984) 276:131-132.*

(Continued)

*Primary Examiner* — Devang Thakor

(74) *Attorney, Agent, or Firm* — Finnegan, Henderson, Farabow, Garrett & Dunner, L.L.P.

(57) ABSTRACT

Compositions and therapeutic kits including an aerosol container containing a foamable composition that includes a nonsteroidal immunomodulating agent are described. The foamable composition includes a liquid hydrophobic carrier; a surface-active agent; polymeric additive; water; and a propellant.

36 Claims, 1 Drawing Sheet

(56) References Cited

U.S. PATENT DOCUMENTS

| | | | |
|---|---|---|---|
| 3,395,215 A | 7/1968 | Warren | |
| 3,401,849 A | 9/1968 | Weber, III | |
| 3,419,658 A | 12/1968 | Amsdon | |
| 3,456,052 A | 7/1969 | Gordon | |
| 3,527,559 A | 9/1970 | Sliwinski | |
| 3,540,448 A | 11/1970 | Sunnen | |
| 3,559,890 A | 2/1971 | Brooks et al. | |
| 3,561,262 A | 2/1971 | Borocki | |
| 3,563,098 A | 2/1971 | Weber, III | |
| 3,574,821 A | 4/1971 | Pfirrmann | |
| 3,577,518 A * | 5/1971 | Shepard | 424/47 |
| 3,667,461 A | 6/1972 | Zamarra | |
| 3,751,562 A | 8/1973 | Nichols | |
| 3,770,648 A * | 11/1973 | Mackles | 516/11 |
| 3,787,566 A * | 1/1974 | Gauvreau | 424/45 |
| 3,819,524 A | 6/1974 | Schubert et al. | |
| 3,824,303 A | 7/1974 | Lanzet et al. | |
| 3,841,525 A | 10/1974 | Siegel | |
| 3,849,569 A | 11/1974 | Mead | |
| 3,849,580 A | 11/1974 | Weinstein et al. | |
| 3,865,275 A | 2/1975 | De Nunzio | |
| 3,866,800 A | 2/1975 | Schmitt | |
| 3,878,118 A | 4/1975 | Watson | |
| 3,882,228 A | 5/1975 | Boncey et al. | |
| 3,886,084 A | 5/1975 | Vassiliades | |
| 3,890,305 A | 6/1975 | Weber et al. | |
| 3,912,665 A | 10/1975 | Spitzer et al. | |
| 3,912,667 A | 10/1975 | Spitzer et al. | |
| 3,923,970 A | 12/1975 | Breuer | |
| 3,929,985 A | 12/1975 | Webb, Jr. | |
| 3,952,916 A | 4/1976 | Phillips | |
| 3,953,591 A | 4/1976 | Snyder | |
| 3,959,160 A | 5/1976 | Horsler et al. | |
| 3,962,150 A * | 6/1976 | Viola | 510/159 |
| 3,963,833 A | 6/1976 | DeSalva et al. | |
| 3,966,090 A | 6/1976 | Prussin et al. | |
| 3,966,632 A | 6/1976 | Colliopoulos et al. | |
| 3,970,219 A | 7/1976 | Spitzer et al. | |
| 3,970,584 A | 7/1976 | Hart et al. | |
| 3,993,224 A | 11/1976 | Harrison | |
| 3,997,467 A | 12/1976 | Jederstrom et al. | |
| 4,001,391 A | 1/1977 | Feinstone et al. | |
| 4,001,442 A | 1/1977 | Stahlberger et al. | |
| 4,018,396 A | 4/1977 | Showmaker et al. | |
| 4,019,657 A | 4/1977 | Spitzer et al. | |
| 4,052,513 A * | 10/1977 | Kaplan | 514/536 |
| 4,083,974 A | 4/1978 | Turi | |
| 4,100,426 A | 7/1978 | Baranowski et al. | |
| 4,102,995 A | 7/1978 | Hebborn | |
| 4,110,426 A | 8/1978 | Barnhurst et al. | |
| 4,124,149 A * | 11/1978 | Spitzer et al. | 222/402.19 |
| 4,145,411 A | 3/1979 | Mende | |
| 4,151,272 A | 4/1979 | Geary et al. | |
| 4,160,827 A | 7/1979 | Cho et al. | |
| 4,178,373 A | 12/1979 | Klein et al. | |
| 4,213,979 A | 7/1980 | Levine | |
| 4,214,000 A | 7/1980 | Papa | |
| 4,226,344 A | 10/1980 | Booth et al. | |
| 4,229,432 A | 10/1980 | Geria | |
| 4,230,701 A | 10/1980 | Holick et al. | |
| 4,241,048 A | 12/1980 | Durbak et al. | |
| 4,241,149 A | 12/1980 | Labes et al. | |
| 4,252,787 A * | 2/1981 | Sherman et al. | 424/45 |
| 4,254,104 A | 3/1981 | Suzuki et al. | |
| 4,268,499 A | 5/1981 | Keil | |
| 4,271,149 A | 6/1981 | Winicov et al. | |
| 4,278,206 A | 7/1981 | Prussin | |
| 4,292,250 A | 9/1981 | DeLuca et al. | |
| 4,292,326 A | 9/1981 | Nazzaro-Porro et al. | |
| 4,299,826 A | 11/1981 | Luedders | |
| 4,305,936 A | 12/1981 | Klein | |
| 4,309,995 A | 1/1982 | Sacco | |
| 4,310,510 A | 1/1982 | Sherman et al. | |
| 4,323,582 A | 4/1982 | Siegel et al. | |
| 4,323,694 A | 4/1982 | Scala, Jr. | |
| 4,325,939 A | 4/1982 | Shah | |
| 4,329,990 A | 5/1982 | Sneider | |
| 4,335,120 A | 6/1982 | Holick et al. | |
| 4,338,211 A | 7/1982 | Stiros | |
| 4,352,808 A | 10/1982 | Rane et al. | |
| 4,363,806 A | 12/1982 | Bergström et al. | |
| 4,385,161 A | 5/1983 | Caunt et al. | |
| 4,386,104 A | 5/1983 | Nazzaro-Porro | |
| 4,393,066 A | 7/1983 | Garrett et al. | |
| 4,427,670 A | 1/1984 | Ofuchi et al. | |
| 4,439,416 A | 3/1984 | Cordon et al. | |
| 4,439,441 A | 3/1984 | Hallesy et al. | |
| 4,440,320 A | 4/1984 | Wernicke | |
| 4,447,486 A | 5/1984 | Hoppe et al. | |
| 4,469,674 A | 9/1984 | Shah et al. | |
| 4,508,705 A | 4/1985 | Chaudhuri et al. | |
| 4,522,948 A | 6/1985 | Walker | |
| 4,529,601 A | 7/1985 | Broberg et al. | |
| 4,529,605 A | 7/1985 | Lynch et al. | |
| 4,552,872 A | 11/1985 | Cooper et al. | |
| 4,574,052 A | 3/1986 | Gupte et al. | |
| 4,576,961 A | 3/1986 | Lorck et al. | |
| 4,595,526 A | 6/1986 | Lai | |
| 4,603,812 A | 8/1986 | Stoesser et al. | |
| 4,607,101 A | 8/1986 | Bernstein | |
| 4,627,973 A | 12/1986 | Moran et al. | |
| 4,628,063 A | 12/1986 | Haines et al. | |
| 4,661,340 A | 4/1987 | Nagy née Kricsfalussy et al. | |
| 4,661,524 A | 4/1987 | Thomson et al. | |
| 4,672,078 A | 6/1987 | Sakai et al. | |
| 4,673,569 A | 6/1987 | Shernov et al. | |
| 4,678,463 A | 7/1987 | Millar | |
| 4,701,320 A | 10/1987 | Hasegawa et al. | |
| 4,725,609 A | 2/1988 | Kull, Jr. et al. | |
| 4,738,396 A | 4/1988 | Doi et al. | |
| 4,741,855 A | 5/1988 | Grote et al. | |
| 4,752,465 A * | 6/1988 | Mackles | 424/45 |
| 4,770,634 A * | 9/1988 | Pellico | 433/217.1 |
| 4,772,427 A | 9/1988 | Dawson | |
| 4,780,309 A | 10/1988 | Geria et al. | |
| 4,784,842 A * | 11/1988 | London et al. | 424/45 |
| 4,792,062 A | 12/1988 | Goncalves | |
| 4,798,682 A | 1/1989 | Ansmann | |
| 4,804,674 A | 2/1989 | Curtis-Prior et al. | |
| 4,806,262 A | 2/1989 | Snyder | |
| 4,808,388 A | 2/1989 | Beutler et al. | |
| 4,822,613 A | 4/1989 | Rodero | |
| 4,822,614 A | 4/1989 | Rodero | |
| 4,826,048 A | 5/1989 | Skorka et al. | |
| 4,827,378 A | 5/1989 | Gillan et al. | |
| 4,828,837 A | 5/1989 | Uster et al. | |
| 4,836,217 A * | 6/1989 | Fischer | 600/556 |
| 4,837,019 A * | 6/1989 | Georgalas et al. | 424/59 |
| 4,837,378 A | 6/1989 | Borgman | |
| 4,844,902 A * | 7/1989 | Grohe | 424/449 |
| 4,847,068 A | 7/1989 | Dole et al. | |
| 4,849,117 A | 7/1989 | Bronner et al. | |
| 4,851,154 A | 7/1989 | Grollier et al. | |
| 4,855,294 A | 8/1989 | Patel et al. | |
| 4,863,900 A | 9/1989 | Pollock et al. | |
| 4,867,967 A | 9/1989 | Crutcher | |
| 4,873,078 A | 10/1989 | Edmundson et al. | |
| 4,874,794 A | 10/1989 | Katz | |
| 4,877,805 A | 10/1989 | Kligman | |
| 4,879,083 A | 11/1989 | Knudson et al. | |
| 4,885,282 A | 12/1989 | Thornfeldt | |
| 4,897,262 A | 1/1990 | Nandagiri et al. | |
| 4,902,281 A | 2/1990 | Avoy | |
| 4,906,453 A | 3/1990 | Tsoucalas | |
| 4,913,893 A | 4/1990 | Varco et al. | |
| 4,919,934 A | 4/1990 | Deckner et al. | |
| 4,933,330 A | 6/1990 | Jorgensen et al. | |
| 4,950,420 A | 8/1990 | Svarz | |
| 4,954,487 A | 9/1990 | Cooper et al. | |
| 4,956,049 A | 9/1990 | Bernheim et al. | |
| 4,957,732 A | 9/1990 | Grollier et al. | |
| 4,963,351 A * | 10/1990 | Weston | 424/73 |
| 4,965,063 A | 10/1990 | Casey et al. | |
| 4,966,779 A | 10/1990 | Kirk | |

(56) References Cited

U.S. PATENT DOCUMENTS

| | | |
|---|---|---|
| 4,970,067 A | 11/1990 | Panandiker et al. |
| 4,975,466 A | 12/1990 | Bottcher et al. |
| 4,981,367 A | 1/1991 | Brazelton |
| 4,981,677 A * | 1/1991 | Thau .............................. 424/45 |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A * | 10/1991 | Mori et al. ................. 424/78.31 |
| 5,071,648 A | 12/1991 | Rosenblatt |
| 5,071,881 A | 12/1991 | Parfondry et al. |
| 5,073,371 A | 12/1991 | Turner et al. |
| 5,082,651 A * | 1/1992 | Healey et al. .................. 424/45 |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A * | 3/1992 | Flynn et al. ................... 514/510 |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,090 A | 4/1993 | Han |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,530 A | 6/1993 | Janchitraponvej et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A * | 1/1995 | Henkin ............................. 514/8 |
| 5,385,943 A | 1/1995 | Nazzaro-Porro |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A * | 9/1995 | Frigerio et al. ................ 424/436 |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,558,872 A | 9/1996 | Jones et al. |
| 5,560,859 A | 10/1996 | Hartmann et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A * | 3/1997 | Clavenna et al. ............... 424/45 |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A * | 7/1997 | Martin ........................ 514/461 |
| 5,650,554 A | 7/1997 | Moloney |
| 5,658,575 A | 8/1997 | Ribier et al. |
| 5,658,749 A * | 8/1997 | Thornton ....................... 435/29 |
| 5,658,956 A | 8/1997 | Martin et al. |
| 5,663,208 A | 9/1997 | Martin |
| 5,672,634 A | 9/1997 | Tseng et al. |
| 5,679,324 A * | 10/1997 | Lisboa et al. .................. 424/45 |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |

(56) References Cited

U.S. PATENT DOCUMENTS

| | | | |
|---|---|---|---|
| 5,753,241 A | 5/1998 | Ribier et al. | |
| 5,753,245 A | 5/1998 | Fowler et al. | |
| 5,753,270 A | 5/1998 | Beauchamp et al. | |
| 5,759,520 A * | 6/1998 | Sachetto | 424/45 |
| 5,759,579 A | 6/1998 | Singh et al. | |
| 5,767,104 A | 6/1998 | Bar-Shalom et al. | |
| 5,773,410 A | 6/1998 | Yamamoto | |
| 5,783,202 A | 7/1998 | Tomlinson et al. | |
| 5,788,664 A | 8/1998 | Scalise | |
| 5,792,448 A | 8/1998 | Dubief et al. | |
| 5,792,922 A | 8/1998 | Moloney et al. | |
| 5,797,955 A | 8/1998 | Walters | |
| 5,804,546 A | 9/1998 | Hall et al. | |
| 5,807,571 A | 9/1998 | List | |
| 5,817,322 A | 10/1998 | Xu et al. | |
| 5,824,650 A | 10/1998 | De Lacharriere et al. | |
| 5,833,960 A | 11/1998 | Gers-Barlag et al. | |
| 5,833,961 A | 11/1998 | Siegfried et al. | |
| 5,837,270 A | 11/1998 | Burgess | |
| 5,840,744 A | 11/1998 | Borgman | |
| 5,840,771 A | 11/1998 | Oldham et al. | |
| 5,843,411 A | 12/1998 | Hernandez et al. | |
| 5,846,983 A | 12/1998 | Sandborn et al. | |
| 5,849,042 A | 12/1998 | Lim et al. | |
| 5,856,452 A | 1/1999 | Moloney et al. | |
| 5,858,371 A | 1/1999 | Singh et al. | |
| 5,865,347 A | 2/1999 | Welschoff | |
| 5,866,040 A | 2/1999 | Nakama et al. | |
| 5,869,529 A | 2/1999 | Sintov et al. | |
| 5,871,720 A | 2/1999 | Gutierrez et al. | |
| 5,877,216 A | 3/1999 | Place et al. | |
| 5,879,469 A | 3/1999 | Avram et al. | |
| 5,881,493 A | 3/1999 | Restive | |
| 5,885,581 A * | 3/1999 | Massand | 424/754 |
| 5,889,028 A | 3/1999 | Sandborn et al. | |
| 5,889,054 A | 3/1999 | Yu et al. | |
| 5,891,458 A | 4/1999 | Britton et al. | |
| 5,902,574 A | 5/1999 | Stoner et al. | |
| 5,902,789 A * | 5/1999 | Stoltz | 514/4 |
| 5,905,092 A | 5/1999 | Osborne et al. | |
| 5,910,382 A | 6/1999 | Goodenough et al. | |
| 5,911,981 A | 6/1999 | Dahms et al. | |
| 5,912,007 A * | 6/1999 | Pan et al. | 424/440 |
| 5,914,122 A * | 6/1999 | Otterbeck et al. | 424/434 |
| 5,914,310 A | 6/1999 | Li et al. | |
| 5,919,830 A | 7/1999 | Gopalkrishnan et al. | |
| 5,922,331 A | 7/1999 | Mausner | |
| 5,925,669 A | 7/1999 | Katz et al. | |
| 5,948,682 A | 9/1999 | Moloney | |
| 5,951,544 A | 9/1999 | Konwitz | |
| 5,951,989 A | 9/1999 | Heymann | |
| 5,951,993 A | 9/1999 | Scholz et al. | |
| 5,952,373 A | 9/1999 | Lanzendorfer et al. | |
| 5,952,392 A | 9/1999 | Katz et al. | |
| 5,955,414 A | 9/1999 | Brown et al. | |
| 5,959,161 A | 9/1999 | Kenmochi et al. | |
| 5,961,957 A | 10/1999 | McAnalley | |
| 5,961,998 A | 10/1999 | Arnaud et al. | |
| 5,972,310 A * | 10/1999 | Sachetto | 424/45 |
| 5,976,555 A | 11/1999 | Liu et al. | |
| 5,980,904 A | 11/1999 | Leverett et al. | |
| 5,990,100 A | 11/1999 | Rosenberg et al. | |
| 5,993,846 A | 11/1999 | Friedman et al. | |
| 6,001,341 A | 12/1999 | Genova et al. | |
| 6,006,948 A | 12/1999 | Auer | |
| 6,019,967 A | 2/2000 | Breton et al. | |
| 6,024,942 A | 2/2000 | Tanner et al. | |
| 6,030,630 A | 2/2000 | Fleury et al. | |
| 6,033,647 A | 3/2000 | Touzan et al. | |
| 6,039,936 A | 3/2000 | Restle et al. | |
| 6,042,848 A | 3/2000 | Lawyer et al. | |
| 6,045,779 A | 4/2000 | Mueller et al. | |
| 6,060,041 A | 5/2000 | Candau et al. | |
| 6,071,536 A | 6/2000 | Suzuki et al. | |
| 6,071,541 A | 6/2000 | Murad | |
| 6,075,056 A | 6/2000 | Quigley, Jr. et al. | |
| 6,080,394 A | 6/2000 | Lin et al. | |
| 6,087,310 A | 7/2000 | Heinkel | |
| 6,087,317 A * | 7/2000 | Gee | 510/417 |
| 6,090,772 A | 7/2000 | Kaiser et al. | |
| 6,093,408 A | 7/2000 | Hasenoehrl et al. | |
| 6,096,756 A | 8/2000 | Crain et al. | |
| 6,110,477 A | 8/2000 | Hernandez et al. | |
| 6,110,966 A | 8/2000 | Pollock | |
| 6,113,888 A | 9/2000 | Castro et al. | |
| 6,116,466 A | 9/2000 | Gueret et al. | |
| 6,121,210 A | 9/2000 | Taylor | |
| 6,126,920 A | 10/2000 | Jones et al. | |
| 6,133,327 A | 10/2000 | Kimura et al. | |
| 6,140,355 A | 10/2000 | Egidio et al. | |
| 6,146,645 A | 11/2000 | Deckers et al. | |
| 6,146,664 A | 11/2000 | Siddiqui | |
| 6,162,834 A | 12/2000 | Sebillotte-Arnaud et al. | |
| 6,165,455 A | 12/2000 | Torgerson et al. | |
| 6,168,576 B1 | 1/2001 | Reynolds | |
| 6,171,347 B1 | 1/2001 | Kunz et al. | |
| 6,180,669 B1 | 1/2001 | Tamarkin | |
| 6,183,762 B1 | 2/2001 | Deckers et al. | |
| 6,186,367 B1 | 2/2001 | Harrold | |
| 6,187,290 B1 | 2/2001 | Gilchrist et al. | |
| 6,189,810 B1 | 2/2001 | Nerushai et al. | |
| 6,190,365 B1 | 2/2001 | Abbott et al. | |
| 6,204,285 B1 | 3/2001 | Fabiano et al. | |
| 6,210,656 B1 | 4/2001 | Touzan et al. | |
| 6,210,742 B1 | 4/2001 | Deckers et al. | |
| 6,214,318 B1 | 4/2001 | Osipow et al. | |
| 6,214,788 B1 | 4/2001 | Velazco et al. | |
| 6,217,887 B1 * | 4/2001 | Beerse et al. | 424/401 |
| 6,221,381 B1 * | 4/2001 | Shelford et al. | 424/442 |
| 6,221,823 B1 | 4/2001 | Crisanti et al. | |
| 6,224,888 B1 | 5/2001 | Vatter et al. | |
| 6,231,837 B1 | 5/2001 | Stroud et al. | |
| 6,232,315 B1 | 5/2001 | Shafer et al. | |
| 6,241,971 B1 | 6/2001 | Fox et al. | |
| 6,251,369 B1 | 6/2001 | Stoltz | |
| 6,258,374 B1 | 7/2001 | Freiss et al. | |
| 6,261,544 B1 | 7/2001 | Coury et al. | |
| 6,270,781 B1 | 8/2001 | Gehlsen | |
| 6,271,295 B1 | 8/2001 | Powell et al. | |
| 6,274,150 B1 | 8/2001 | Simonnet et al. | |
| 6,283,336 B1 | 9/2001 | Dwyer et al. | |
| 6,284,802 B1 | 9/2001 | Bissett et al. | |
| 6,287,546 B1 | 9/2001 | Reich et al. | |
| 6,294,550 B1 | 9/2001 | Place et al. | |
| 6,299,023 B1 | 10/2001 | Arnone | |
| 6,299,032 B1 | 10/2001 | Hamilton | |
| 6,299,900 B1 | 10/2001 | Reed et al. | |
| 6,305,578 B1 | 10/2001 | Hildebrandt et al. | |
| 6,306,841 B1 | 10/2001 | Place et al. | |
| 6,308,863 B1 | 10/2001 | Harman | |
| 6,319,913 B1 | 11/2001 | Mak et al. | |
| 6,328,950 B1 | 12/2001 | Franzke et al. | |
| 6,328,982 B1 | 12/2001 | Shiroyama et al. | |
| 6,333,362 B1 | 12/2001 | Lorant | |
| 6,335,022 B1 | 1/2002 | Simonnet et al. | |
| 6,341,717 B2 | 1/2002 | Auer | |
| 6,344,218 B1 | 2/2002 | Dodd et al. | |
| 6,348,229 B1 | 2/2002 | Eini et al. | |
| 6,355,230 B2 | 3/2002 | Gers-Barlag et al. | |
| 6,358,541 B1 | 3/2002 | Goodman | |
| 6,358,924 B1 | 3/2002 | Hoffmann | |
| 6,364,854 B1 | 4/2002 | Ferrer et al. | |
| 6,372,234 B1 | 4/2002 | Deckers et al. | |
| 6,375,936 B1 | 4/2002 | Allard et al. | |
| 6,375,960 B1 | 4/2002 | Simonnet et al. | |
| 6,383,471 B1 | 5/2002 | Chen et al. | |
| 6,395,258 B1 | 5/2002 | Steer | |
| 6,395,300 B1 | 5/2002 | Straub et al. | |
| 6,403,061 B1 | 6/2002 | Candau et al. | |
| 6,403,069 B1 | 6/2002 | Chopra et al. | |
| 6,410,036 B1 | 6/2002 | De Rosa et al. | |
| 6,423,323 B2 | 7/2002 | Neubourg | |
| 6,423,329 B1 | 7/2002 | Sine et al. | |
| 6,428,772 B1 | 8/2002 | Singh et al. | |

(56) References Cited

U.S. PATENT DOCUMENTS

| | | |
|---|---|---|
| 6,433,003 B1 | 8/2002 | Bobrove et al. |
| 6,433,024 B1 | 8/2002 | Popp et al. |
| 6,433,033 B1 | 8/2002 | Isobe et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang |
| 6,479,058 B1 | 11/2002 | McCadden |
| 6,479,060 B1 | 11/2002 | Jones et al. |
| 6,479,532 B1 | 11/2002 | Kamimura et al. |
| 6,482,810 B1 | 11/2002 | Brem et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,551,604 B1 | 4/2003 | Beck et al. |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,607,716 B1 | 8/2003 | Smith et al. |
| 6,610,315 B2 | 8/2003 | Scholz et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,706,290 B1 | 3/2004 | Kajander et al. |
| 6,709,663 B2 | 3/2004 | Espinoza |
| 6,723,309 B1 | 4/2004 | Deane |
| 6,730,288 B1 | 5/2004 | Abram |
| 6,736,860 B2 | 5/2004 | Patel et al. |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,841,547 B2 | 1/2005 | Brown et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin et al. |
| 6,911,211 B2 | 6/2005 | Eini et al. |
| 6,914,057 B1 | 7/2005 | Ryan et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,986,883 B2 | 1/2006 | Pellico |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram et al. |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Mekata |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,842,791 B2 | 11/2010 | Britten et al. |
| 7,960,416 B2 | 6/2011 | Sato et al. |
| 8,114,385 B2 | 2/2012 | Tamarkin et al. |
| 8,119,106 B2 | 2/2012 | Tamarkin et al. |
| 8,119,109 B2 | 2/2012 | Tamarkin et al. |
| 8,158,109 B2 | 4/2012 | Abram et al. |
| 8,192,749 B2 | 6/2012 | Ashley |
| 8,211,874 B2 | 7/2012 | Theobald et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,374 B2 | 7/2013 | Tamarkin et al. |
| 8,486,375 B2 | 7/2013 | Tamarkin et al. |
| 8,486,376 B2 | 7/2013 | Friedman et al. |
| 8,512,718 B2 | 8/2013 | Eini et al. |
| 8,518,376 B2 | 8/2013 | Tamarkin et al. |
| 8,518,378 B2 | 8/2013 | Tamarkin et al. |
| 8,592,380 B2 | 11/2013 | Trumbore et al. |
| 8,617,100 B2 | 12/2013 | Eini et al. |
| 8,618,081 B2 | 12/2013 | Tamarkin et al. |
| 8,623,330 B2 | 1/2014 | Gurge et al. |
| 8,636,982 B2 | 1/2014 | Tamarkin et al. |
| 8,652,443 B2 | 2/2014 | Varanasi et al. |
| 8,709,385 B2 | 4/2014 | Tamarkin et al. |
| 8,722,021 B2 | 5/2014 | Friedman et al. |
| 8,735,377 B1 | 5/2014 | Sipos |
| 8,741,265 B2 | 6/2014 | Tamarkin et al. |
| 8,784,780 B2 | 7/2014 | Gurge et al. |
| 8,846,039 B2 | 9/2014 | Chung et al. |
| 8,895,536 B2 | 11/2014 | Bannister et al. |
| 8,992,896 B2 | 3/2015 | Tamarkin et al. |
| 9,050,253 B2 | 6/2015 | Tamarkin et al. |
| 9,101,662 B2 | 8/2015 | Tamarkin et al. |
| 9,192,558 B2 | 11/2015 | Chen et al. |
| 2001/0006654 A1 | 7/2001 | Cannell et al. |
| 2001/0026790 A1 | 10/2001 | Gers-Barlag et al. |
| 2001/0027218 A1 | 10/2001 | Stern et al. |
| 2001/0027981 A1 | 10/2001 | Yquel |
| 2001/0033838 A1 | 10/2001 | Farmer |
| 2001/0036450 A1 | 11/2001 | Verite et al. |
| 2001/0054574 A1 | 12/2001 | Navarro |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0031478 A1 | 3/2002 | Keller et al. |
| 2002/0032171 A1* | 3/2002 | Chen et al. ............ 514/54 |

(56) References Cited

U.S. PATENT DOCUMENTS

| | | |
|---|---|---|
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Halswanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0182234 A1 | 12/2002 | Riedel et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0013692 A1 | 1/2003 | Gullans et al. |
| 2003/0017181 A1 | 1/2003 | Rood et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0077301 A1 | 4/2003 | Maibach et al. |
| 2003/0078172 A1 | 4/2003 | Guiramand et al. |
| 2003/0082120 A1 | 5/2003 | Milstein |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0118527 A1 | 6/2003 | Jager et al. |
| 2003/0129259 A1 | 7/2003 | Mahalingam et al. |
| 2003/0130247 A1 | 7/2003 | Gans et al. |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0185861 A1 | 10/2003 | Hori et al. |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215418 A1 | 11/2003 | Asmus et al. |
| 2003/0215472 A1 | 11/2003 | Bonda et al. |
| 2003/0235597 A1 | 12/2003 | Withiam et al. |
| 2004/0002550 A1 | 1/2004 | Mercurio |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0198706 A1 | 10/2004 | Carrara |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0258628 A1 | 12/2004 | Riedel et al. |
| 2004/0258643 A1 | 12/2004 | Yaqub et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |
| 2005/0031547 A1 | 2/2005 | Tamarkin et al. |
| 2005/0042182 A1 | 2/2005 | Arkin |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0084551 A1* | 4/2005 | Jensen et al. .................. 424/769 |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0148552 A1 | 7/2005 | Ryan et al. |
| 2005/0153943 A1 | 7/2005 | Ashley |
| 2005/0164993 A1 | 7/2005 | Ashley |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1* | 1/2006 | Friedman et al. ............ 424/401 |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Meketa |
| 2006/0057168 A1 | 3/2006 | Larm |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |

(56) References Cited

U.S. PATENT DOCUMENTS

| | | |
|---|---|---|
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0015739 A1 | 1/2007 | Walker et al. |
| 2007/0017696 A1 | 1/2007 | Lin et al. |
| 2007/0020213 A1 | 1/2007 | Tamarkin |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0053943 A1 | 3/2007 | Wang et al. |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0111956 A1 | 5/2007 | Matsushima et al. |
| 2007/0134174 A1 | 6/2007 | Irwin et al. |
| 2007/0140998 A1 | 6/2007 | Kato et al. |
| 2007/0140999 A1 | 6/2007 | Puglia et al. |
| 2007/0141086 A1 | 6/2007 | Ohara et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0166274 A1 | 7/2007 | Mazur et al. |
| 2007/0224143 A1 | 9/2007 | Konis |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0017147 A1 | 1/2009 | Lintner et al. |
| 2009/0041680 A1 | 2/2009 | Tamarkin et al. |
| 2009/0053290 A1 | 2/2009 | Sand et al. |
| 2009/0061001 A1 | 3/2009 | Hougaz |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0214628 A1 | 8/2009 | De Rijk |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0137198 A1 | 6/2010 | Eini et al. |
| 2010/0221194 A1 | 9/2010 | Loupenok |
| 2010/0221195 A1 | 9/2010 | Tamarkin et al. |
| 2010/0247449 A1 | 9/2010 | Graupe et al. |
| 2010/0266510 A1 | 10/2010 | Tamarkin et al. |
| 2010/0286417 A1 | 11/2010 | Mendes et al. |
| 2011/0002857 A1 | 1/2011 | Tamarkin et al. |
| 2011/0002969 A1 | 1/2011 | Serraima et al. |
| 2011/0008266 A1 | 1/2011 | Tamarkin et al. |
| 2011/0045037 A1 | 2/2011 | Tamarkin et al. |
| 2011/0097279 A1 | 4/2011 | Tamarkin et al. |
| 2011/0212033 A1 | 9/2011 | Tamarkin et al. |
| 2011/0262542 A1 | 10/2011 | Ashley |
| 2011/0268665 A1 | 11/2011 | Tamarkin et al. |
| 2012/0064136 A1 | 3/2012 | Baker, Jr. et al. |
| 2012/0082632 A1 | 4/2012 | Phillips et al. |
| 2012/0087872 A1 | 4/2012 | Tamarkin et al. |
| 2012/0128598 A1 | 5/2012 | Trumbore et al. |
| 2012/0141384 A1 | 6/2012 | Tamarkin |
| 2012/0148503 A1 | 6/2012 | Tamarkin et al. |
| 2012/0156144 A1 | 6/2012 | Tamarkin et al. |
| 2012/0164087 A1 | 6/2012 | Carter |
| 2012/0181201 A1 | 7/2012 | Heggie |
| 2012/0195836 A1 | 8/2012 | Tamarkin et al. |
| 2012/0213709 A1 | 8/2012 | Tamarkin et al. |
| 2012/0213710 A1 | 8/2012 | Tamarkin et al. |
| 2012/0237453 A1 | 9/2012 | Tamarkin et al. |
| 2013/0011342 A1 | 1/2013 | Tamarkin et al. |
| 2013/0028850 A1 | 1/2013 | Tamarkin et al. |
| 2013/0053353 A1 | 2/2013 | Tamarkin et al. |
| 2013/0064777 A1 | 3/2013 | Tamarkin et al. |
| 2013/0115173 A1 | 5/2013 | Trumbore et al. |
| 2013/0161351 A1 | 6/2013 | Eini et al. |
| 2013/0164225 A1 | 6/2013 | Tamarkin et al. |
| 2013/0183250 A1 | 7/2013 | Friedman et al. |
| 2013/0183251 A1 | 7/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0189196 A1 | 7/2013 | Tamarkin et al. |
| 2013/0195769 A1 | 8/2013 | Tamarkin et al. |
| 2013/0225536 A1 | 8/2013 | Tamarkin et al. |
| 2013/0251644 A1 | 9/2013 | Majhi et al. |
| 2013/0261565 A1 | 10/2013 | Wong et al. |
| 2013/0295022 A1 | 11/2013 | Friedman et al. |
| 2013/0296387 A1 | 11/2013 | Saad |
| 2014/0050673 A1 | 2/2014 | Tamarkin et al. |
| 2014/0066524 A1 | 3/2014 | Tamarkin et al. |
| 2014/0086848 A1 | 3/2014 | Tamarkin et al. |
| 2014/0121188 A1 | 5/2014 | Tamarkin et al. |
| 2014/0140937 A1 | 5/2014 | Gurge et al. |
| 2014/0147504 A1 | 5/2014 | Salman et al. |
| 2014/0182585 A1 | 7/2014 | Tamarkin et al. |
| 2014/0186269 A1 | 7/2014 | Tamarkin et al. |
| 2014/0186442 A1 | 7/2014 | Mansouri |
| 2014/0193502 A1 | 7/2014 | Tamarkin et al. |
| 2014/0221320 A1 | 8/2014 | Joks et al. |
| 2014/0227199 A1 | 8/2014 | Tamarkin et al. |
| 2014/0228355 A1 | 8/2014 | Kortagere et al. |
| 2014/0248219 A1 | 9/2014 | Tamarkin et al. |
| 2014/0271494 A1 | 9/2014 | Tamarkin et al. |
| 2015/0025060 A1 | 1/2015 | Tamarkin et al. |
| 2015/0098907 A1 | 4/2015 | Tamarkin et al. |
| 2015/0118164 A1 | 4/2015 | Tamarkin et al. |

(56) References Cited

U.S. PATENT DOCUMENTS

| | | |
|---|---|---|
| 2015/0125496 A1 | 5/2015 | Yamamoto |
| 2015/0141381 A1 | 5/2015 | Levy et al. |
| 2015/0157586 A1 | 6/2015 | Tamarkin et al. |
| 2015/0164922 A1 | 6/2015 | Tamarkin et al. |
| 2015/0174144 A1 | 6/2015 | Bowser et al. |
| 2015/0190409 A1 | 7/2015 | Tamarkin et al. |
| 2015/0196570 A1 | 7/2015 | Tamarkin et al. |
| 2015/0209296 A1 | 7/2015 | Yamamoto |
| 2015/0374625 A1 | 12/2015 | Tamarkin et al. |
| 2016/0101051 A1 | 4/2016 | Tamarkin et al. |
| 2016/0101184 A1 | 4/2016 | Tamarkin et al. |
| 2016/0158261 A1 | 6/2016 | Friedman et al. |

FOREIGN PATENT DOCUMENTS

| | | | |
|---|---|---|---|
| AU | 2010219295 | 9/2012 | |
| CA | 2114537 | 2/1993 | |
| CA | 2154438 | 1/1996 | |
| CA | 2422244 | 9/2003 | |
| CA | 2502986 | 8/2011 | |
| CA | 2534372 | 1/2012 | |
| CA | 2536482 | 7/2012 | |
| CH | 639913 | 12/1983 | |
| DE | 933486 | 9/1955 | |
| DE | 1 882 100 | 11/1963 | |
| DE | 1926796 | 11/1965 | |
| DE | 4140474 | 6/1993 | |
| DE | 10009233 | 8/2000 | |
| DE | 10138495 | 2/2003 | |
| DE | 102004016710 | 10/2005 | |
| DE | 2 608 226 | 9/2007 | |
| EP | 52404 | 5/1982 | |
| EP | 0156507 A1 | 10/1985 | |
| EP | 0186453 | * 12/1985 | |
| EP | 211550 | 2/1987 | |
| EP | 0 213 827 | 3/1987 | |
| EP | 0214865 A2 | 3/1987 | |
| EP | 0 216 856 | 4/1987 | |
| EP | 0270316 | 8/1988 | |
| EP | 297436 | 1/1989 | |
| EP | 0 326 196 | 8/1989 | |
| EP | 0 336 812 | 10/1989 | |
| EP | 0 391 124 | 10/1990 | |
| EP | 0404376 | 12/1990 | |
| EP | 414920 | 3/1991 | |
| EP | 0 485 299 | 5/1992 | |
| EP | 0484530 A1 | 5/1992 | |
| EP | 0488089 A1 | 6/1992 | |
| EP | 0 504 301 | 9/1992 | |
| EP | 0 528 190 | 2/1993 | |
| EP | 0 552 612 | 7/1993 | |
| EP | 0535327 | 7/1993 | |
| EP | 0569773 A2 | 11/1993 | |
| EP | 0598412 | 11/1993 | |
| EP | 0 662 431 | 7/1995 | |
| EP | 0676198 | 10/1995 | |
| EP | 0738516 | 10/1996 | |
| EP | 0 757 959 | 2/1997 | |
| EP | 0824911 | 2/1998 | |
| EP | 0 829 259 | 3/1998 | |
| EP | 0 928 608 | 7/1999 | |
| EP | 0 979 654 | 2/2000 | |
| EP | 0993827 A1 | 4/2000 | |
| EP | 1 025 836 | 8/2000 | |
| EP | 1055425 A2 | 11/2000 | |
| EP | 0 506 197 | 7/2001 | |
| EP | 1215258 | 6/2002 | |
| EP | 1287813 | 3/2003 | |
| EP | 1 308 169 | 5/2003 | |
| EP | 1 375 386 | 1/2004 | |
| EP | 1428521 | 6/2004 | |
| EP | 1438946 | 7/2004 | |
| EP | 1189579 | 9/2004 | |
| EP | 1475381 | 11/2004 | |
| EP | 1 483 001 | 12/2004 | |
| EP | 1 500 385 | 1/2005 | |
| EP | 1500385 | 1/2005 | |
| EP | 1 537 916 | 6/2005 | |
| EP | 1 600 185 | 11/2005 | |
| EP | 1 653 932 | 5/2006 | |
| EP | 1 734 927 | 12/2006 | |
| EP | 1 758 547 | 3/2007 | |
| EP | 1584324 | 11/2007 | |
| EP | 1 889 609 | 2/2008 | |
| EP | 1 902 706 | 3/2008 | |
| EP | 2 129 383 | 12/2009 | |
| EP | 2422768 | 2/2012 | |
| EP | 2494959 | 9/2012 | |
| FR | 2 456 522 | 12/1980 | |
| FR | 2 591 331 | 6/1987 | |
| FR | 2 640 942 | 6/1990 | |
| FR | 2 736 824 | 1/1997 | |
| FR | 2 774 595 | 8/1999 | |
| FR | 2 789 371 | 8/2000 | |
| FR | 2 793 479 | 11/2000 | |
| FR | 2 814 959 | 4/2002 | |
| FR | 2 833 246 | 6/2003 | |
| FR | 2 840 903 | 12/2003 | |
| FR | 2 843 373 | 2/2004 | |
| FR | 2 845 672 | 4/2004 | |
| FR | 2 848 998 | 6/2004 | |
| FR | 2 860 976 | 4/2005 | |
| FR | 2915891 | 11/2008 | |
| GB | 808104 | 1/1959 | |
| GB | 808105 | 1/1959 | |
| GB | 922930 | 4/1963 | |
| GB | 933 486 | 8/1963 | |
| GB | 998 490 | 7/1965 | |
| GB | 1026831 | 4/1966 | |
| GB | 1 033 299 | 6/1966 | |
| GB | 1 081 949 | 9/1967 | |
| GB | 1121358 | 7/1968 | |
| GB | 1 162 684 | 8/1969 | |
| GB | 1 170 152 | 11/1969 | |
| GB | 1 201 918 | 8/1970 | |
| GB | 1 347 950 | 2/1974 | |
| GB | 1 351 761 | 5/1974 | |
| GB | 1 351 762 | 5/1974 | |
| GB | 1 353 381 | 5/1974 | |
| GB | 1 376 649 | 12/1974 | |
| GB | 1397285 | 6/1975 | |
| GB | 1 408 036 | 10/1975 | |
| GB | 1 457 671 | 12/1976 | |
| GB | 1489672 | * 10/1977 | ............... A61K 7/16 |
| GB | 2 004 746 | 4/1979 | |
| GB | 1 561 423 | 2/1980 | |
| GB | 2114580 | 8/1983 | |
| GB | 2 153 686 | 8/1985 | |
| GB | 2 172 298 | 9/1986 | |
| GB | 2 206 099 | 12/1988 | |
| GB | 2166651 | 5/1996 | |
| GB | 2337461 | 11/1999 | |
| GB | 2 367 809 | 4/2002 | |
| GB | 2 406 330 | 3/2005 | |
| GB | 2 406 791 | 4/2005 | |
| GB | 2 474 930 | 7/2012 | |
| IL | 49491 | 9/1979 | |
| IL | 0152486 | 5/2003 | |
| JP | 60001113 | 4/1978 | |
| JP | 55069682 | 5/1980 | |
| JP | 57044429 | 3/1982 | |
| JP | 56039815 | 4/1984 | |
| JP | 61275395 | 12/1986 | |
| JP | 62241701 | 10/1987 | |
| JP | 63119420 | 5/1988 | |
| JP | 01100111 | 4/1989 | |
| JP | 01156906 | 6/1989 | |
| JP | 2184614 | 7/1990 | |
| JP | 2255890 | 10/1990 | |
| JP | 04282311 | 10/1992 | |
| JP | 4312521 | 11/1992 | |
| JP | 5070340 | 3/1993 | |
| JP | 5213734 | 8/1993 | |
| JP | 6100414 | 4/1994 | |

(56) References Cited

FOREIGN PATENT DOCUMENTS

| | | |
|---|---|---|
| JP | H06-263630 | 6/1994 |
| JP | 6329532 | 11/1994 |
| JP | 2007/155667 | 6/1995 |
| JP | 7215835 | 8/1995 |
| JP | 8501529 | 2/1996 |
| JP | 2008040899 | 2/1996 |
| JP | 8119831 | 5/1996 |
| JP | 8165218 | 6/1996 |
| JP | 8277209 | 10/1996 |
| JP | 09 084855 | 3/1997 |
| JP | 9099553 | 4/1997 |
| JP | 9110636 | 4/1997 |
| JP | 10114619 | 5/1998 |
| JP | 3050289 | 9/1998 |
| JP | 2010/332456 | 12/1998 |
| JP | 11501045 | 1/1999 |
| JP | 11250543 | 9/1999 |
| JP | 2000/017174 | 1/2000 |
| JP | 2000080017 | 3/2000 |
| JP | 2000128734 | 5/2000 |
| JP | 2000191429 | 7/2000 |
| JP | 2000239140 | 9/2000 |
| JP | 2000/354623 | 12/2000 |
| JP | 2000351726 | 12/2000 |
| JP | 2001/002526 | 1/2001 |
| JP | 2001019606 | 1/2001 |
| JP | 2001072963 | 3/2001 |
| JP | 2002012513 | 1/2002 |
| JP | 2002047136 | 2/2002 |
| JP | 2002/524490 | 8/2002 |
| JP | 2002/302419 | 10/2002 |
| JP | 2003/012511 | 1/2003 |
| JP | 2003055146 | 2/2003 |
| JP | 2004/047136 | 2/2004 |
| JP | 2004/250435 | 9/2004 |
| JP | 2004/348277 | 12/2004 |
| JP | 2005/314323 | 11/2005 |
| JP | 2005350378 | 12/2005 |
| JP | 2006008574 | 1/2006 |
| JP | 2006/036317 | 2/2006 |
| JP | 2006/103799 | 4/2006 |
| JP | 2006525145 | 11/2006 |
| JP | 2007131539 | 5/2007 |
| JP | 2007326996 | 12/2007 |
| KR | 143232 | 7/1998 |
| KR | 2001/003063 | 1/2001 |
| NZ | 520014 | 5/2005 |
| NZ | 540166 | 6/2007 |
| RU | 2277501 | 6/2006 |
| UA | 66796 | 6/2004 |
| WO | 82/01821 | 6/1982 |
| WO | WO-86/05389 | 9/1986 |
| WO | 88/01502 | 3/1988 |
| WO | WO-88/01863 | 3/1988 |
| WO | 88/08316 | 11/1988 |
| WO | WO-89/06537 | 7/1989 |
| WO | WO-90/05774 | 5/1990 |
| WO | WO-91/11991 | 8/1991 |
| WO | WO 91/11991 | 8/1991 |
| WO | WO-92/00077 | 1/1992 |
| WO | JP 4-51958 | 2/1992 |
| WO | 92/05142 | 4/1992 |
| WO | 92/05763 | 4/1992 |
| WO | WO-92/11839 | 7/1992 |
| WO | WO 92/13602 | 8/1992 |
| WO | 93/25189 | 12/1993 |
| WO | 94/06440 | 3/1994 |
| WO | WO-96/03115 | 2/1996 |
| WO | WO 96/19921 | 4/1996 |
| WO | 96/24325 | 8/1996 |
| WO | 96/26711 | 9/1996 |
| WO | WO 96/27376 | 9/1996 |
| WO | WO-96/39119 | 12/1996 |
| WO | 97/03638 | 2/1997 |
| WO | 97/39745 | 10/1997 |
| WO | 98/17282 | 4/1998 |
| WO | WO-98/18472 | 5/1998 |
| WO | WO-98/19654 | 5/1998 |
| WO | WO-98/21955 | 5/1998 |
| WO | WO-98/23291 | 6/1998 |
| WO | WO 98/31339 | 7/1998 |
| WO | WO-98/36733 | 8/1998 |
| WO | 98/52536 | 11/1998 |
| WO | WO-99/08649 | 2/1999 |
| WO | WO-99/20250 | 4/1999 |
| WO | WO-99/37282 | 7/1999 |
| WO | 99/53923 | 10/1999 |
| WO | WO-00/09082 | 2/2000 |
| WO | WO 00/15193 * | 3/2000 ............ A61K 9/12 |
| WO | 00/23051 | 4/2000 |
| WO | WO 00/62776 | 4/2000 |
| WO | 00/33825 | 6/2000 |
| WO | 00/38731 | 7/2000 |
| WO | WO-00/61076 | 10/2000 |
| WO | WO 00/72805 | 12/2000 |
| WO | WO-00/76461 | 12/2000 |
| WO | 01/05366 | 1/2001 |
| WO | WO 01/01949 | 1/2001 |
| WO | 01/10961 | 2/2001 |
| WO | WO-01/08681 | 2/2001 |
| WO | 01/53198 | 7/2001 |
| WO | 01/54212 | 7/2001 |
| WO | WO-01/54679 | 8/2001 |
| WO | WO 01/62209 * | 8/2001 ............ A61K 7/00 |
| WO | WO 01/70242 A2 | 9/2001 |
| WO | 01/82880 | 11/2001 |
| WO | 01/82890 | 11/2001 |
| WO | 01/85102 | 11/2001 |
| WO | 01/85128 | 11/2001 |
| WO | 01/95728 | 12/2001 |
| WO | WO-02/00820 | 1/2002 |
| WO | WO 02/07685 | 1/2002 |
| WO | 02/15860 | 2/2002 |
| WO | 02/15873 | 2/2002 |
| WO | WO 02/24161 | 3/2002 |
| WO | WO-02/28435 | 4/2002 |
| WO | WO 02/41847 | 5/2002 |
| WO | WO-02/43490 | 6/2002 |
| WO | WO-02/062324 | 8/2002 |
| WO | 02/078667 | 10/2002 |
| WO | 02/087519 | 11/2002 |
| WO | 03/000223 | 1/2003 |
| WO | 03/002082 | 1/2003 |
| WO | WO 03/005985 | 1/2003 |
| WO | 03/013984 | 2/2003 |
| WO | WO 03/015699 | 2/2003 |
| WO | WO 03/051294 | 6/2003 |
| WO | 03/055454 | 7/2003 |
| WO | WO-03/053292 | 7/2003 |
| WO | WO-03/055445 | 7/2003 |
| WO | 03/070301 | 8/2003 |
| WO | 03/071995 | 9/2003 |
| WO | WO-03/075851 | 9/2003 |
| WO | 03/097002 | 11/2003 |
| WO | WO-03/092641 | 11/2003 |
| WO | WO 03/094873 | 11/2003 |
| WO | WO03/094873 | 11/2003 |
| WO | 2004/017962 | 3/2004 |
| WO | 2004/037197 | 5/2004 |
| WO | WO 2004/037225 A2 | 5/2004 |
| WO | 2004/003284 | 8/2004 |
| WO | 2004/064769 | 8/2004 |
| WO | WO-2004/064833 A1 | 8/2004 |
| WO | WO-2004/071479 A1 | 8/2004 |
| WO | 2004/078158 | 9/2004 |
| WO | WO-2004/078896 | 9/2004 |
| WO | 2004/093895 | 11/2004 |
| WO | WO 2004/112780 A1 | 12/2004 |
| WO | WO-2005/011567 A2 | 2/2005 |
| WO | WO-2005/018530 | 3/2005 |
| WO | WO-2005/018530 A2 | 3/2005 |
| WO | WO-2005/032522 | 4/2005 |

(56) References Cited

FOREIGN PATENT DOCUMENTS

| | | |
|---|---|---|
| WO | WO-2005/044219 | 5/2005 |
| WO | 2005/063224 | 7/2005 |
| WO | WO-2005/065652 | 7/2005 |
| WO | WO-2005/076697 | 8/2005 |
| WO | WO-2005/097068 A1 | 10/2005 |
| WO | 2005/102282 | 11/2005 |
| WO | 2005/102539 | 11/2005 |
| WO | WO-2005/117813 | 12/2005 |
| WO | WO-2006/003481 A2 | 1/2006 |
| WO | 2006/011046 | 2/2006 |
| WO | WO-2006/010589 | 2/2006 |
| WO | WO 2006/020682 | 2/2006 |
| WO | 2006/028339 | 3/2006 |
| WO | WO-2006/031271 | 3/2006 |
| WO | 2006/045170 | 5/2006 |
| WO | 2006/079632 | 8/2006 |
| WO | 2006/081327 | 8/2006 |
| WO | 2006/091229 | 8/2006 |
| WO | WO-2006/091229 | 8/2006 |
| WO | WO-2006/100485 | 9/2006 |
| WO | 2006/121610 | 11/2006 |
| WO | 2006/122158 | 11/2006 |
| WO | WO-2006/120682 | 11/2006 |
| WO | WO-2006/129161 | 12/2006 |
| WO | WO-2006/131784 | 12/2006 |
| WO | WO-2007/007208 | 1/2007 |
| WO | WO 2007/010494 | 1/2007 |
| WO | WO-2007/012977 | 2/2007 |
| WO | WO-2007/023396 | 3/2007 |
| WO | WO-2007/031621 A2 | 3/2007 |
| WO | WO-2007/039825 | 4/2007 |
| WO | WO-2007/050543 | 5/2007 |
| WO | WO-2007/054818 | 5/2007 |
| WO | WO-2007/072216 | 6/2007 |
| WO | WO 2007/082698 | 7/2007 |
| WO | WO-2007/085899 | 8/2007 |
| WO | WO-2007/085902 | 8/2007 |
| WO | WO-2007/099396 | 9/2007 |
| WO | 2007/111962 | 10/2007 |
| WO | 2008/010963 | 1/2008 |
| WO | WO-2008/008397 | 1/2008 |
| WO | 2008/041045 | 4/2008 |
| WO | WO-2008/038147 | 4/2008 |
| WO | WO-2008/075207 | 6/2008 |
| WO | WO-2008/087148 | 7/2008 |
| WO | WO 2008/104734 | 9/2008 |
| WO | WO-2008/110872 A2 | 9/2008 |
| WO | 2008/152444 | 12/2008 |
| WO | WO 2008/152444 | 12/2008 |
| WO | WO-2009/007785 A2 | 1/2009 |
| WO | WO-2009/069006 A2 | 6/2009 |
| WO | WO-2009/072007 A2 | 6/2009 |
| WO | WO-2009/087578 A2 | 7/2009 |
| WO | WO-2009/090495 A2 | 7/2009 |
| WO | WO-2009/090558 A2 | 7/2009 |
| WO | WO-2009/098595 A2 | 8/2009 |
| WO | WO 2011/006026 | 1/2011 |
| WO | WO 2011/026094 | 3/2011 |
| WO | 2011/039637 | 4/2011 |
| WO | 2011/039638 | 4/2011 |
| WO | WO 2011/064631 | 6/2011 |
| WO | WO 2011/106026 | 9/2011 |
| WO | WO 2011/138678 | 11/2011 |
| WO | WO 2013/136192 | 9/2013 |
| WO | WO 2014/134394 | 9/2014 |
| WO | WO 2014/134427 | 9/2014 |
| WO | WO 2014/151347 | 9/2014 |
| WO | WO 2014/201541 | 12/2014 |
| WO | WO 2005/009416 | 2/2015 |
| WO | WO 2015/075640 | 5/2015 |
| WO | WO 2015/114320 | 8/2015 |
| WO | WO 2015/153864 | 10/2015 |

OTHER PUBLICATIONS

Hakan. The Turkish Journal of Gastroenterology. 2000, vol. 11, No. 2, pp. 155-161.*
Encyclopedia of Pharmaceutical Technology ,Second Edition, vol. 3. Copyright 2002. Editors: James Swarbrick and James C. Boylan.*
Bioadhesive Drug Delivery. In Water-Soluble Polymers. Leung and Robinson. Copyright 1991.*
Characteristics of Surfactants and Emulsions. http://web.archive.org/web/20000106225413/http://pharmacy.wilkes.edu/kibbeweb/lab7.html. Archived Jan. 6, 2000. Accessed Jan. 29, 2010.*
Kanamoto. J. Pharmacobiodyn. Mar. 1988;11(3):141-5.*
AG&Co. http://www.agworkshop.com/p3.asp.*
Emulsifiers. Aug. 31, 2007, [online], [retrieved Jun. 1, 2011], Retrieved from Internet <URL:http://www.theherbarie.com/files/resource-center/formulating/Emulsifiers_HLB_Values.pdf> in view of U.S. Pat. No. 5,679,324 (Lisaboa, Oct. 21, 1997).*
Indomethacin. Aug. 15, 2009, [online] [retrieved Jun. 3, 2011] Retrieved from Internet <URL:http://it03.net/com/oxymatrine/down/1249534834.pdf>.*
Tavss (J. Soc. Cosmet. Chem. 3, 9, 267-272 (Jul./Aug. 1988).*
Barry, B.W. et al, Comparative bio-availability and activity of proprietary topical corticosteroid preparations: vasoconstrictor assays on thirty-one ointments, British Journal of Dermatology, 93, 563-571, 1975.
Tamarkin, D., et al. Body Cavity Foam, U.S. Appl. No. 11/116,761, filed Apr. 28, 2005.
Tamarkin, D., et al. Moisturizing Foam Containing Lanolin, U.S. Appl. No. 11/099,942, filed Apr. 6, 2005.
Tamarkin, D., et al. Steroid Kit and Foamable Composition and Uses, U.S. Appl. No. 11/114,410, filed Apr. 26, 2005.
Tamarkin, D., et al. Vasoactive Kit and Composition and Uses Thereof, U.S. Appl. No. 11/124,676, filed May 9, 2005.
Martindale, The extra pharmacopoeia [28th] edition, Eds.: Reynolds, J.E.F. and Prasad, A.B., The Pharmaceutical Press, London, 1982, pp. 862-864.
Tamarkin, D. et al., *Foam Carrier Containing Amphiphilic Copolymer Gelling Agent*, filed Aug. 4, 2004, U.S. Appl. No. 10/911,367.
Tamarkin, D. et al., *Foam Incorporating Eutectic Mixture*, filed Aug. 20, 2004, U.S. Appl. No. 10/922,555.
Tamarkin, D., et al. *Oleaginous Pharmaceutical and Cosmetic Foam*, filed Apr. 28, 2004, U.S. Appl. No. 10/835,505.
Tamarkin, D., et al. *Penetrating Pharmaceutical Foam*, filed Aug. 20, 2004, U.S. Appl. No. 10/922,358.
Wormser et al. Arch. Toxicol., 1997, 71, 165-170.
Wormser et al. *Letters to the* Editor, Burns, 1998, 24, 383.
Alcohol SDA 40B.http://www.pharmco-prod.com/pages/MSDS/SDA_40B_200.pdf Accessed Dec. 9, 2008, 2 pages.
Ambrose, Ursual et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.
Arisan, http://www.arisankimya.com/kozmetik.htm Accessed Dec. 10, 2008.
Benet, et al., Application of NMR for the Determination of HLB Values of Nonionic Surfactants, Journal of the American Oil Chemists Society, vol. 49, 1972, 499-500.
Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.
Carbowax 1000MSDS; http://www.sciencelab.com/xMSDS-Polyethylene_glycol_1000-9926622. Accessed Dec. 13, 2008, 6 pages.
Cheshire, et al., Disorders of Sweating, www.medscape.com, Semin Neurol 23(4):399-406, 2003.
Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.
D.W.A. Sharp Dictionary of Chemistry, Penguin Books, 1983, 3 pages.

(56) References Cited

OTHER PUBLICATIONS

Dalby, "Determination of Drug Solubility in Aerosol Propellants," Pharmaceutical Research, vol. 8, No. 9, 1991, pp. 1206-1209.
Denatonium Benzoate http://www.newdruginfo.com/pharmaceopeia/usp28/v28230/usp28nf23s0_m22790.htm Accessed Dec. 9, 2008.
Emulsifiers with HLB values. http://www.theherbarie.com/files/resources-center/formulating/Emulsifiers_HLB_Values.pdf accessed Aug. 5, 2009 (3 pps).
Ethanol, Accessed http://www.sigmaaldrich.com/catalog/ProductDetail.do?N4=E7023SIAL&N5=SEARCH_CONCAT_PNOBRAND_KEY&F=SPEC Dec. 9, 2008, 2 pages.
European Patent Application No. 06831721, Official Action, Feb. 3, 2009, 9 pages.
Flick, Cosmetic and Toiletry Formulations, vol. 5, 2nd Edition, Copyright 1996.
Fontana, Anthony, J., "Water Activity: Why It Is Important for Food Safety," International Conference on Food Safety, Nov. 16-18, 1998, 9 pages.
Galligan, John et al., "Adhesive Polyurethane Liners for Anterior Restorations," J. Dent. Res., Jul.-Aug., 1968, pp. 629-632.
Gill, A.M, et al., "Adverse Drug Reactions in a Paediatric Intensitve Care Unit," Acta Paediatr 84:438-441, 1995.
Hall, Karla, "Diaper Area Hemanglomas: A Unique Set of Concerns," http://members.tripod.com/~Michelle_G/diaper.html, Dec. 1, 2008, 8 pages.
International Search Report and Written Opinion, International Application No. PCT/IB2006/003628, Foamix Ltd., Dec. 7, 2007, 15 pages.
International Search Report and Written Opinion, International Application No. PCT/US2007/004459, Foamix Ltd., Dec. 9, 2008, 2 pages.
International Search Report for International Application No. PCT/IB2006/003974, Feb. 25, 2008 (3 pages).
International Search Report, International Patent Application No. PCT/IB2007/003463, Foamix, Ltd., Jul. 18, 2008, 3 pages.
International Search Report, International Patent Application No. PCT/IB2007/003759, Foamix Ltd., Jul. 8, 2008 (3 pages).
Kathon™ CG (product information sheet by Rohm and Haas, Jun. 2006).
Kinnunen, Contact Dermatitis Sep. 1989; 21(3): 154-8.
Licking Vaginal Dryness without a Prescription. Accessed http://www.estronaut.com/a/vag_dryness.htm on Dec. 14, 2008.
Merriam-Webster Online Dictionaary, 2008, "Mousse," Merriam-Webster Online, Dec. 8, 2008 http://www.merriam-webster.com/dictionary/mousse.
OM Cinnamate. http://www.makingcosmetics.com/sunscreens/OM-Cinnamate-p102.html accessed Sep. 26, 2009.
Pendergrass, "The shape and dimensions of the human vagina as seen in three-dimensional vinyl polysiloxane casts," Gynecol Obstet. Invest. 1996:42(3):178-82 (abstract).
Progesterone MSDS. http://www.usp.org.pdf.EN/referenceStandards/msds/1568007.pdf on Dec. 14, 2002, 5 pages.
Scott as Published in Pharmaceutical Dosage Forms; Disperse Systems, vol. 3, Copyright 1998.
Sigma Aldrich, "HLB-Numbers in Lithography Nanopatterning," http://www.sigmaaldrich.com/materials-science/micro-and-nanoelectronics/lithography-nanopatterning/hlb-numbers.html, accessed: Feb. 2, 2009, pp. 1-3.
Skin Biology, CP Serum—Copper-Peptide Serum for Skin Regeneration and Reducing Wrinkles, Skin Biology, http;//web.archive.org/web/20030810230608/http://www.skinbio.com/cpserum.html, Dec. 1, 2008, 21 pages.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).

Edirisinghe, et al., "Effect of fatty acids on endothelium-dependent relaxation in the rabbit aorta", Clin Sci (Lond). Aug. 2006; 111(2): 145-51.
Encyclopedia of Pharmaceutical Technology, Second Edition, vol. 3, Copyright 2002.
http://ibabydoc.com/online/diseaseeczema.asp., Atopic Dermatitis, Copyright 2000.
http://www.agworkshop.com/p3.asp, AG&Co. Essential oil workshop.
MMP Inc. International Development and Manufacturing, "Formulating specialities," http://mmpinc.com.
Tarumoto, et al., Studies on toxicity of hydrocortisone 17-butyrate 21-propionate-1. Accute toxicity of hydrocortisone 17-butyrate 21-propionate and its analogues in mice, rats and dogs (author's trans), J Toxicol Sci., Jul. 1981; 6 Suppl: 1-16.
U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 8, 2010, Tamarkin.
U.S. Appl. No. 61/363,577, filed Jul. 12, 2010, Eini.
Final Office Action for U.S. Appl. No. 11/430,437, Tamarkin et al., Dec. 16, 2008, 24 pages.
Fontana, Anthony J., "Water Activity: Why It is Important for Food Safety," International Conference on Food Safety, Nov. 16-18, 1998, pp. 177-185.
Gallarate, et al., "On the Stability of Ascorbic Acid in Emulsified Systems for Topical and Cosmetic Use", International Journal of Pharmaceutics, 188:233-241 (1999).
Gill, A.M, et al., "Adverse Drug Reactions in a Paediatric Intensive Care Unit," Acta Paediatr 84:438-441, 1995.
Gladkikh, "Ascorbic Acid and Methods of Increasing its Stability in Drugs", Translated from Khimiko-Farmatsevticheskii Zhurnal, 4(12):37-42 (1970)—1 page.
Glaser, et al., Hyperhidrosis: A Comprehensive and Practical Approach to Patient Management, Expert Rev. Dermatol. 1(6), 773-775 (2006).
Graves, S. et al. "Structure of Concentrated Nanoemulsions." The Journal of Chemical Physics. 122 America Institute of Physics. Published Apr. 1, 2005. 6 pages.
Groveman, et al., "Lack of Efficacy of Polysorbate 60 in the Treatment of Male Pattern Baldness", Arch Intern Med, 145:1454-1458 (1985).
Gschnait, F., et al., "Topical Indomethacin Protects from UVB and UVA Irriadiation," Arch. Dermatol. Res. 276:131-132, 1984.
Hakan, et al., "The protective effect of fish oil enema in acetic acid and ethanol induced colitis," The Turkish Journal of Gasroenterology, 2000, vol. 11, No. 2, pp. 155-161.
Hall, Karla, "Diaper Area Hemangiomas: A Unique Set of Concerns," http://members.tripod.com/.about.Michelle.sub.--G/diaper.html, Dec. 1, 2008, 8 pages.
Hallstar. Retrieved online on Jun. 4, 2011. <URL:http://www.hallstar.com/pis.php?product=1H022>. 1 page.
Hargreaves, "Chemical Formulation, An Overview of Surfactant-Based Preparations Used in Everyday Life", *The Royal Society of Chemistry*, pp. 114-115 (2003).
Harrison, et al., "Effects of cytokines and R-837, a cytokine inducer, on UV-irradiation augmented recurrent genital herpes in guinea pigs", Antivial Res., 15(4):315-322 (1991).
Harrison, et al., "Modification of Immunological Responses and Clinical Disease During Topical R-837 Treatment of Genital HSV-2 Infection", Antiviral Research, 10:209-224 (1988).
Harrison, et al., "Pharmacokinetics and Safety of Imiquimod 5% Cream in the Treatment of Actinic Keratoses of the Face, Scalp, or Hands and Arms", Arch. Dermatol. Res., 296(1):6-11 (2004)—Abstract, 1 page.
Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).
Hashim, et al. "Tinea versicolor and visceral leishmaniasis," Int J Dermatol., Apr. 1994; 33(4), pp. 258-259 (abstract only).

(56) References Cited

OTHER PUBLICATIONS

Heart Failure, The Merck Manual, 2008 <<http://www.merck.com/mmhe/sec03/ch025/ch025a.html>> 12 pages.
Hepburn, NC., "Cutaneous leishmaniasis," Clin Exp Dermatol, Jul. 2000; 25(5), pp. 363-370 (abstract only).
Hill, Randall M. (Ed.) Silicone Surfactants, Table of Contents and Chapter 7, "Silicone Surfactants: Applicants in the Personal Care Industry," by David T. Floyd, 1999 (30 Pages).
Hormones. Http://www.greenwillowtree.com/Page.bok?file=libido.html. Jan. 2001.
http://ibabydoc.com/online/diseaseeczema.asp., Atopic Dermatitis, Copyright 2000, 6 pages.
http://web.archive.org/web/20000106225413/http://pharmacy.wilkes.edu/kibbeweb/lab7.html, Characteristics of Surfactants and Emulsions, Jan. 29, 2010, 5 pages.
http://www.agworkshop.com/p3.asp, AG&Co. Essential oil workshop. 1 page. Accessed Jan. 31, 2010.
Hubbe, Martin. Mini-Encyclopedia of Papermaking Wet-End Chemistry: Additives and Ingredients, their Composition, Functions, Strategies for Use. Retrieved online on Jun. 4, 2011. <URL:// http://www4.ncsu.edu/~hubbe/CSIL.htm>. Feb. 1, 2001. 2 pages.
Hydroxyethylcellulose. Http: //terpconnect.umd.edu/-choi/MSDS/Sigma-Aldrich/HYDROXYETHYL%20CELLULOSE, 5 pages, Jan. 14, 2004.
ICI Americas Inc. "The HLB System: A Time-Saving Guide to Emulsifier Selection." Mar. 1980. pp. 1-22.
Ikuta, et al., "Scanning Electron Microscopic Observation of Oil/Wax/Water/Surfacant System", Journal of SCCJ, 34(4):280-291 (2004)—Abstract, 1 page.
Indomethacin. Retrieved online on Jun. 3, 2011. <URL:http://it03.net/com/oxymatrine/down/1249534834.pdf>. Aug. 15, 2009. 3 pages.
Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.
Izquierdo, P. et al. "Formation and Stability of Nano-Emulsions Prepared Using the Phase Inversion Temperature Method." University of Barcelona. Sep. 17, 2001. 1 page.
Jan. "Troubled Times: Detergent Foam." http://zetatalk.com/health/theall7c.htm. Accessed Feb. 9, 2012. 2 pages.
Joseph, "Understanding foams & foaming," University of Minnesota (1997), at http://www.aem.umn.edu/people/faculty/joseph/archive/docs/understandingfoams.pdf, pp. 1-8.
Kalkan, et al., The Measurement of Sweat Intensity Using a New Technique, Tr. J. of Medical Sciences 28, 515-517 (1998).
Kanamoto, et al., "Pharmacokinetics of two rectal dosage forms of ketoprofen in patients after anal surgery," J Pharmacobiodyn., Mar. 1988; 11(3):141-5.
Kang,et al., "Enhancement of the Stability and Skin Penetration of Vitamin C by Polyphenol", Immune Netw., 4(4):250-254 (2004)—Abstract, 1 page.
Karasu, T.B. et al., "Treatment of Patients with Major Depressive Disorder, Second Edition," pp. 1-78, 2000.
Kathon.TM. CG (product information sheet by Rohm and Haas, Jun. 2006).
Kim, "Stability of Minoxidil in Aqueous Solution", Yakhak Hoechi, 30(5):228-231 (1986)—Abstract, 1 page.
Kinnunen, "Skin reactions to hexylene glycol," Contact Dermatitis Sep. 1989; 21(3): 154-8.
Kleber, M.D., H.D. et al., "Treatment of Patients with Substance Use Disorders, Second Edition," pp. 1-276, 2006.
Koerber, S., "Humectants and Water Activity," Water Activity News, 2000, ISSN No. 1083-3943.
Kreuter, J. "Nanoparticles and microparticles for drug and vaccine delivery," J. Anat. (1996) 189, pp. 503-505.
Kumar, J. et ak., "Application of Broad Spectrum Antiseptic Povidone Iodine as Powerful Action: A Review," Journal of Pharmaceutical Science and Technology vol. 1(2), 2009, 48-58.

Kwak et al. "Study of Complete Transparent Nano-Emulsions which Contain Oils." IFSCC Conference 2003, Seoul, Korea, Sep. 22-24, 2003. 3 pages.
Lautenschlager, Dr. Hans. "A Closer Look on Natural Agents: Facts and Future Aspects." Kosmetic Konzept. Kosmetische Praxis. 2006 (no month given). (5), 8-10. 3 pages.
Lebwohl et al. "Treatment of Psoriasis. Part 1. Topical Therapy and Phototherapy." J. Am. Acad. Dermatol. 45:487-498. Oct. 2001.
Lebwohl et al., "A randomized, double-blind, placebo-controlled study of clobestasol propionate 0.05% foam in the treatment of nonscalp psoriasis," International Journal of Dermatology, 2002, 41(5): 269-274.
Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).
Leung, et al., "Bioadhesive Drug Delivery in Water-Soluble Polymers," American Chemical Society, Chapter 23, 1991, pp. 350-366.
Li, et al., "Solubility Behavior of Imiquimod in Alkanoic Acids", Abstract 3029, Pharmaceutical Research, vol. 14, No. 11 Supplemental (November), p. S475 (1997), 2 pages.
Licking Vaginal Dryness without a Prescription. Accessed http://www.estronaut.com/a/vag.sub.--dryness.htm on Dec. 14, 2008, 3 pages.
Lippacher, A. et al. "Liquid and Semisolid SLN Dispersions for Topical Application" Rheological Characterization. European Journal of Pharmaceutics and Biopharmaceutics. 58. 2004. pp. 561-567.
Lupo, "Antioxidants and Vitamins in Cosmetics", Clinics in Dermatology, 19:467-473 (2001).
Martindale, The extra pharmacopoeia [28th] edition, Eds.: Reynolds, J.E.F. and Prasad, A.B., The Pharmaceutical Press, London, pp. 862-864, 1982.
Martindale. 33 ed. London, Bath Press, 2002. pp. 1073 and 1473.
Material Safety Data Sheet, Progesterone, Apr. 26, 2006, 5 pages.
Material Safety Data Sheet, Science Lab.com, Polyethylene Glycol 1000, MSDS, Nov. 6, 2008, 6 pages.
Merck index, 10th edition, Merck & Co., Inc.: Rahway, NJ, 1983, pp. 39 (entry 242 for allantoin).
Merck index, 14th edition, O'Neill, ed., 2006, entry for p-amino benzoic acid.
Merck index, 14th edition, O'Neill, ed., 2006, entry for zinc oxide.
Merck Manual Home Edition. "Excessive Sweating: Sweating Disorders." Accessed Apr. 14, 2011 at www.merckmanuals.com/home/print/sec18/ch206/ch206c.html. 2 pages.
Merriam Webster Online Dictionary [online] retrieved from http://www.merriam-webster.com/cgi-bin/dictionary?book=dictionary&va=derivative on Jul. 5, 2008; 1 page.
Merriam-Webster Online Dictionaary, 2008, "Mousse," Merriam-Webster Online, Dec. 8, 2008 http://www.merriam-webster.com/dictionary/mousse, 2 pages.
Messenger, et al., "Minoxidil: Mechanisms of Action on Hair Growth", British Journal of Dermatology, 150:186-194 (2004).
Metronidazole. www.usp.org/pdf/EN/veterinary/metronidazole.pdf. accessed Sep. 10, 2009, 4 pages.
Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3-4):147-153 (1985)—Abstract, 1 page.
MMP Inc. International Development and Manufacturing, "Formulating specialities," http://mmpinc.com, 3 pages. Feb. 2, 2010.
Molan, Peter Clark, "World Wide Wounds," Dec. 2001, 13 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
Neutrogena. Http://www.cosmetoscope.com/2010/04/neutrogea-clinical-with-johnson-johnsons-cytomimic-techology/. Published Apr. 28, 2010. Accessed Sep. 11, 2010, 5 pages.
Nietz, "Molecular orientation at surfaces of solids," J. Phys. Chem., 1928, 32(2): 255-269.
No Author Listed. "Opitmization of Nano-Emulsions Production by Microfluidization." European Food Research and Technology. vol. 225, No. 5-6. Sep. 2007. Abstract. 1 page.

(56) References Cited

OTHER PUBLICATIONS

Office Action for U.S. Appl. No. 11/430,437, Tamarkin et al., May 9, 2008, 27 pages.
Office Action received from the U.S. Patent Office, U.S. Appl. No. 11/430,599, Jul. 28, 2008 (59 pages).
Oil. Dictionary of Chemistry. Editor: DWA Sharp. Copyright 1990.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
OM Cinnamate. http://www.makingcosmetics.com/sunscreens/OM-Cinnamate-p102.html accessed Sep. 26, 2009, 1 page.
Padhi et al., "Phospho-olicines as positive-electrode materials for rechargeable lithium batteries," J. Electrochemical Soc., 1997, 144(4): 1188-1194.
Pakpayat, et al., "Formulation of Ascorbic Acid Microemulstions with Alkyl Polyglycosides", European Journal of Pharmaceutics and Biopharmaceutics, 72:444-452 (2009).
Paula. http://ww.cosmeticscop.com/cosmetic-ingredient-dictionary/definition/259/c12-15-alkyl-benzoate.aspx. Printed Oct. 24, 2010. 1 page.
Pendergrass, "The shape and dimension of the human vagina as seen in three-dimensional vinyl polysiloxane casts," Gynecol Obstet. Invest. 1996:42(3):178-82.
Prescription Information for Aldara, Mar. 2007 (29 pages).
Prevent. (2007). In The American Heritage Dictionary of the English Language. Retrieved from http://www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural Jojoba Oil Versus Dryness and Free Radicals." Cosmetics and Toiletries Manufacture Worldwide. 1988. 4 pages.
Raschke, et al., "Topical Activity of Ascorbic Acid: From In Vitro Optimization to In Vivo Efficacy", Skin Pharmacology and Physiology, 17(4):200-206 (2004)—Abstract, 1 page.
Ravet et al., "Electroactivity of natural and synthetic triphylite," J. of Power Sources, 2001, 97-98: 503-507.
Raymond, Iodine as an Aerial Disinfectant, Journal of Hygiene, vol. 44, No. 5 (May 1946), pp. 359-361.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Rosacea, http://clinuvel.com/skin-conditions/common-skin-conditions/rosacea#h0-6-prevention. Accessed Sep. 9, 2010, 5 pages.
Savin, et al., "Tinea versicolor treated with terbinafine 1% solution," Int J. Dermatol, Nov. 1999; 38(11), pp. 863-865.
Schmidt A., "Malassezia furfur: a fungus belonging to the physiological skin flora and its relevance in skin disorders," Curtis., Jan. 1997; 59(1), pp. 21-24 (abstract).
Schulze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Scott as Published in Pharmaceutical Dosage Forms; Disperse Systems, vol. 3, Copyright 1998, 120 pages.
Seborrheic Dermatitis, http://www.cumc.columbia.edu/student/health/pdf/R-S/Seborrhea%20Dermatitis.pdf. Access Sep. 9, 2010, 2 pages.
Shear, et al., "Pharmacoeconomic analysis of topical treatments for tinea infections," Pharmacoeconomics. Mar. 1995; 7(3); pp. 251-267 (abstract only).
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.

Shim, et al., "Transdermal Delivery of Mixnoxidil with Block Copolymer Nanoparticles", J. Control Release, 97(3):477-484 (2004)—Abstract, 1 page.
Shrestha et al., Forming properties of monoglycerol fatty acid esters in nonpolar oil systems, Langmuir, 2006, 22: 8337-8345.
Sigma Aldrich, "HLB-Numbers in Lithography Nanopatterning," http://www.sigmaaldrich.com/materials-science/micro-and-nanoelectronics/l- ithography-nanopatterning/hlb-numbers.html, accessed: Feb. 2, 2009, pp. 1-3.
Sigma-Aldrich, Material Safety Data Sheet, Hydroxyethyl Cellulose, Mar. 3, 2004, 5 pages.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen OTR-2NF)," International Journal of Cosmetic Science, vol. 2(2): abstract only. Dec. 24, 2001, 1 page.
Skin Biology, CP Serum—Copper-Peptide Serum for Skin Regeneration and Reducing Wrinkles, Skin Biology, http;//web.archive.org/web/20030810230608/http://www.skinbio.com/cpserum.-html, Dec. 1, 2008, 21 pages.
Skin Deep Cosmetics. PPG-40-PEG-60 Lanolin Oil http://www.cosmeticsdatabase.com/ingredient/722972/PPG-40-PEG-60_Lanolin_Oil/?ingred06=722972. 2010, 3 pages.
Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.
Sonneville-Aubrun, O. et al. "Nanoemulsions: A New Vehicle for Skincare Products." Advances in Colloid and Interface Science. 108-109.. 2004. pp. 145-149.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).
Sreenivasa, et al., "Preparation and Evaluation of Minoxidil Gels for Topical Application in Alopecia", Indian Journal of Pharmaceutical Sciences, 68(4):432-436 (2006), 11 pages.
Stehle et al., Uptake of minoxidil from a new foam formulation devoid of propylene glycol to hamster ear hair follicles, J. Invest. Dermatol., 2005, 124(4), A101.
Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.
Surfactant. Chemistry Glossary. Http://chemistry.about.com/od/chemistryglossary/g/surfactant.htm, 2012, 1 page.
Sweetman, Sean C. Martindale: The Complete Drug Reference. 33rd Edition. London. Pharmaceutical Press. Jun. 21, 2002. pags. 1073 and 1473. 5 pages.
Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.
Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.
Tanhehco, "Potassium Channel Modulators as Anti-Inflammatory Agents", Expert Opinion on Therapeutic Patents, 11(7):1137-1145 (2001)—Abstract, 3 pages.
Tarumoto, et al., Studies on toxicity of hydrocortisone 17-butyrate 21-propionate-1. Accute toxicity of hydrocortisone 17-butyrate 21-propionate and its analogues in mice, rats and dogs (author's trans), J Toxicol Sci., Jul. 1981; 6 Suppl: 1-16 (Abstract only).
Tata, et al., "Penetration of Minoxidil from Ethanol Propylene Glycol Solutions: Effect of Application Volume on Occlusion", Journal of Pharmaceutical Sciences, 84(6):688-691 (1995).
Tata, et al., "Relative Influence of Ethanol and Propylene Glycol Cosolvents on Deposition of Minoxidil into the Skin", Journal of Pharmaceutical Sciences, 83(10):1508-1510 (1994).
Third Party Submission for U.S. Appl. No. 12/014,088, filed Feb. 4, 2009, 4 pages, cited by other.

(56) References Cited

OTHER PUBLICATIONS

Torres-Rodriguez, JM., "New topical antifungal drugs," Arch Med Res. 1993 Winter; 24(4), pp. 371-375 (abstract).
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.
Trofatter, "Imiquimod in clinical Practice", European Journal of Dermatology, 8(7 Supp.):17-19 (1998)—Abstract, 1 page.
Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.
Tsai, et al., "Effect of Minoxidil Concentration on the Deposition of Drug and Vehicle into the Skin", International Journal of Pharmaceutics, 96(1-3):111-117 (1993)—Abstract, 1 page.
Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).
Tyring, "Immune-Response Modifiers: A New Paradigm in the Treatment of Human Papillomavirus", Current Therapeutic Research, 61(9):584-596 (2000)—Abstract, 1 page.
Tzen, Jason T.C. et al. "Surface Structure and Properties of Plant Seed Oil Bodies." Department of Botany and Plant Sciences, University of California, Riverside, California 92521. Apr. 15, 1992. 9 pages.
Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.
Veron, et al., "Stability of Minoxidil Topical Formulations", Ciencia Pharmaceutica, 2(6):411-414 (1992), Abstract, 1 page.
Wermuth, C.G. "Similarity in drugs: reflections on analogue design," Drug Discovery Today, vol. 11, Nos. 7/8, Apr. 2006, pp. 348-354.
Williams, "Scale up of an olive/water cream containing 40% diethylene glycol momoethyl ether", Dev. Ind. Pharm., 26(1):71-77 (2000).
Wormser et al., Protective effect of povidone-iodine ointment against skin lesions induced by sulphur and nitrogen mustards and by non-mustard vesicants, Arch. Toxicol., 1997, 71, 165-170.
Wormser, Early topical treatment with providone-iodine ointment reduces, and sometimes prevents, skin damage following heat stimulus, Letter to the Editor, Burns 24, pp. 383, 1998.
Yamada and Chung, "Crystal Chemistry of the Olivine-Type Li(Mn$_y$Fe$_{l-y}$)PO$_4$ and (Mn$_y$Fe$_{l-y}$)PO$_4$ as Possible 4 V Cathode Materials for Lithium Batteries," J. Electrochemical Soc., 2001, 148(8): A960-967.
"Coal tars and coal-tar pitches," Report on Carcinogens, Twelfth Edition, 2011, 3 pages.
Adisen et al. "Topical tetracycline in the treatment of acne vulgaris," J Drugs Dermatol., 2008, 7:953-5.
Baskaran et al., "Poloxamer-188 improves capillary blood flow and tissue viability in a cutaneous burn wound," J. Surg. Res., 2001, 101(1):56-61.
Bell-Syer et al. "A systematic review of oral treatments for fungal infections of the skin of the feet," J. Dermatolog. Treat., 2001, 12:69-74.
Boehm et al. 1994, "Synthesis of high specific activity [.sup.3 H]-9-cis-retinoic acid and its application for identifying retinoids with unusual binding properties," J. Med. Chem., 37:408-414;.
Carapeti et al., "Topical diltiazem and bethanechol decrease anal sphincter pressure and heal anal fissures without side effects," Dis Colon Rectum, 2000, 43(10):1359-62.
Cook and Mortensen, "Nifedipine for treatment of anal fissures," Dis Colon Rectum, 2000, 43(3):430-1.
Dumortier et al., "A review of poloxamer 407 pharmaceutical and pharmacological characteristics," Pharmaceutical Res., 2006, 23(12):2709-2728.

Ebadi et al., "Healing effect of topical nifedipine on skin wounds of diabetic rats," DARU, 2003, 11(1):19-22.
Effendy and Maibach. "Surfactants and Experimental Irritant Contact Dermatitis." Contact Dermatol., 1995, 33:217-225.
Elias and Ghadially, "The aged epidermal permeability barrier," Clinical Geriatric Medicine, Feb. 2002, pp. 103-120.
Fantin et al., "Critical influence of resistance to streptogramin B-type antibiotics on activity of RP 59500 (Quinupristin-dalfopristin) in experimental endocarditis due to Staphylococcus aureus," Antimicrob Agents and Chemothery, 1999, 39:400-405.
Fluhr et al., "Glycerol accelerates recovery of barrier function in vivo," Acta Derm. Venereol,. 1999, 79:418-21.
Garti et al. "Sucrose Esters microemulsions," J. Molec. Liquids, 1999, 80:253-296.
Hammer et al. "Anti-Microbial Activity of Essential Oils and other Plant extracts," J. Applied. Microbiology, 1999, 86:985-990.
Hwang et al. "Isolation and identification of mosquito repellents in Artemisia vulgaris," J. Chem. Ecol., 11: 1297-1306, 1985.
Knight et al., "Topical diltiazem ointment in the treatment of chronic anal fissure," Br. J. Surg., 2001, 88(4):553-6.
Kucharekova et al., "Effect of a lipid-rich emollient containing ceramide 3 in experimentally induced skin barrier dysfunction," Contact Dermatitis, Jun. 2002, pp. 331-338.
Leive et al, "Tetracyclines of various hydrophobicities as a probe for permeability of Escherichia coli outer membrane," Antimicrobial Agents and Chemotherapy, 1984, 25:539-544.
Luepke and Kemper, "The HET-CAM Test: An Alternative to the Draize Eye Test," FD Chem. Toxic., 1986, 24:495-196.
Osborne and Henke, "Skin Penetration Enhancers Cited in the Technical Literature," Pharm. Technology, Nov. 1997, pp. 58-86.
Padi. "Minocycline prevents the development of neuropathic pain, but not acute pain: possible anti-inflammatory and antioxidant mechanisms," Eur J. Pharmacol, 2008, 601:79-87.
Palamaras and Kyriakis, "Calcium antagonists in dermatology: a review of the evidence and research-based studies," Derm. Online Journal, 2005, 11(2):8.
Passi et al., Lipophilic antioxidants in human sebum and aging, Free Radical Research, 2002, pp. 471-477.
Perrotti et al., "Topical Nifedipine With Lidocaine Ointment vs. Active Control for Treatment of Chronic Anal Fissure," Dis Colon Rectum, 2002, 45(11):1468-1475.
Repa et al. "All-trans-retinol is a ligand for the retinoic acid receptors," Proc. Natl. Acad Sci, USA, 90: 7293-7297, 1993.
Ruledge, "Some corrections to the record on insect repellents and attractants," J. Am. Mosquito Control Assoc, 1988, 4(4): 414-425.
Sakai et al., "Characterization of the physical properties of the stratum corneum by a new tactile sensor," Skin Research and Technology, Aug. 2000, pp. 128-134.
Schaefer, "Silicone Surfactants," Tenside, Surfactants, Deterg., 1990, 27(3): 154-158.
Simoni et al., "Retinoic acid and analogs as potent inducers of differentiation and apoptosis. New promising chemopreventive and chemotherapeutic agents in oncology," Pure Appl Chem., 2001, 73(9):1437-1444.
Smith, "Hydroxy acids and skin again," Soap Cosmetics Chemical Specialties, 1993, pp. 54-59.
Solans et al. "Overview of basic aspects of microemulsions," Industrial Applications of Microemulsions, Solans et al Eds, New York, 1997, 66:1-17.
Squillante et al., "Codiffusion of propylene glycol and dimethyl isosorbide in hairless mouse skin," European J. Pharm. Biopharm., 1998, 46(3):265-71.
Todd et al. "Volatile Silicone Fluids for Cosmetics," 91 Cosmetics and Toiletries, 1976, 27-32.
Torma et al., "Biologic activities of retinoic acid and 3, 4-dehydroretinoic acid in human keratinoacytes are similar and correlate with receptor affinities and transactivation properties," J. Invest. Dermatology, 1994, 102: 49-54.
USP23/NF 18 The United States Pharmacopeia: The National Formulary, US Pharmacopoeia, 1995, p. 10-14.

(56) References Cited

OTHER PUBLICATIONS

Van Slyke, "On the measurement of buffer values and on the relationship of buffer value to the dissociation constant of the buffer and the concentration and reaction of the buffer solution," *J. Biol. Chem.*, 1922, 52:525-570.
Van Cutsem et al., "The antiinflammatory efects of ketoconazole," *J. Am. Acad. Dermatol.*,1991, 25(2 pt 1):257-261.
Wang and Chen, "Preparation and surface active properties of biodegradable dextrin derivative surfactants," *Colloids and Surfaces A: Physicochemical and Engineering Aspects*, 2006, 281(1-3): 190-193.
Weindl et al., "Hyaluronic acid in the treatment and prevention of skin diseases: molecular biological, pharmaceutical and clinical aspects," *Skin Pharmacology and Physiology*, 2004, 17: 207-213.
Xynos et al., "Effect of nifedipine on rectoanal motility," *Dis Colon Rectum*, 1996, 39(2):212-216.
Yamada et al., "Candesartan, an angiotensin II receptor antagonist, suppresses pancreatic inflammation and fibrosis in rats," *J. Pharmacol. Exp. Ther.*, 2003, 307(1)17-23.
Paragraph E.3.1 of regulation (EC) No. 2003 (See Directive 67/548/ EEC OJ 196, 16.8, 1967, p. 1.
Tzen et al., Lipids, proteins and structure of seed oil bodies from diverse species; *Plant Physiol.*, 1993, 101:267-276.
Brown et al. "Structural dependence of flavonoid interactions with Cu2+ inos: implications for their antioxidant properties," *Biochem. J.*, 1998, 330:1173-1178.
"Mineral oil USP," Chemical Abstracts Service Registry No. 8012-95-1, 2011, 7 pages.
"Tea tree oil," Chemical Abstract No. 68647-73-4, 2012, 2 pages.
Lin et al., "Ferulic acid stabilizes a solution of vitamins c and e and doubles its photoprotection of skin," *J Invest Dermatol*, 2005, 125:826-32.
International Preliminary Report on Patentability from PCT/ IB2006/002755 dated, Sep. 12, 2012, 8 pages; International Search Report dated, May 30, 2007, 4 pages.
"Arquad HTL8-MS,"*AkzoNobel Functional Applications*, retrieved on Mar. 18, 2013, Retrieved from the Internet: <URL: http://sc.akzonobel.com/en/fa/Pages/product-detail.aspx?prodID=8764>, 1 page.
"Burn patients need vitamin D supplements." *Decision News Media*, Jan. 23, 2004, http://www.nutraingredients.com/Research/ Burn-patients-need-vitamin-D-supplements, Accessed: May 5, 2010.
"Can tuberous sclerosis be prevented?," *Sharecare*, 2002, retrieved on Aug. 29, 2013, <URL: http://www.sharecare.com/health/ autosomal-dominant-genetic-disorders/can-tuberous-sclerosis-be-prevented;jsessionid=850579B60520A907DE75930E061E60E6>, 2 pages.
"Crohn's Disease," *Merch Manual Home Edition*, retrieved on Jan. 16, 2013, <http://www.merckmanuals.com/home/digestive_disorders/inflammatory_bowel_diseases_ibd/crohn_disease. html?qt=crohn's disease&alt=sh>, 3 pages.
"Dacarbazine," *Chemical Book*, 2010, retrieved on Oct. 18, 2013, <URL: http://www.chemicalbook.com/ChemicalProductProperty_ EN_CB7710656.htm>, 2 pages.
"Drug Index (Professional)—Dacarbazine," *BC Cancer Agency*, Jun. 2004, retrieved on Oct. 18, 2013, <URL:http://www.bccancer. bc.ca/HPI/DrugDatabase/DrugIndexPro/Dacarbazine.htm>, 6 pages.
"Fully refined paraffin waxes (FRP Wax)," *Industrial Raw Materials LLC*, Feb. 21, 2008, retrieved on Aug. 22, 2013, <http://irmwax. com/Wax/Paraffin/fully_refined.asp> 1 page.
"Gas Gangrene," Merch Manual Home Edition, 2008, retrieved on Jan. 16, 2013, <http://www.merckmanuals.com/home/infections/ bacterial_infections/gas_gangrene.html?qt=gasgangrene &alt=sh>1 page.
"HLB Systems", http://pharmcal.tripod.com/ch17.htm, Accessed Sep. 17, 2010, pp. 1-3.
"Human Immunodeficiency Virus Infection," Merch Manual Home Edition, 2008, retrieved on Jan. 16, 2013, <http://www.merckmanuals.com/home/infections/human_immunodeficiency_virus_hiv_ infection/human_immunodeficiency_virus_infection. html?qt=human immunodeficiency virus infection&alt=sh>, 11 pages.
"Minocycline (DB01017)," *DrugBank*, Feb. 8, 2013, retrieved on Aug. 15, 2013, <http://www.drugbank.ca/drugs/DB01017>, 10 pages.
"Minocycline" accessed on Oct. 21, 2011 at en.wikipedia.org/wiki/ Minocycline, 7 pages.
"New Nanomaterials to deliver anticancer drugs to cells developed," *Science Daily*, Jun. 2007, retrieved on Oct. 14, 2013, <URL: http://www.sciencedaily.com/releases/2007/06/070607112931. htm>, 3 pages.
"Product Data Sheet for Meclocycline," *bioaustralis fine chemicals*, Jun. 28, 2013, 1 page.
"Reaction Rate" Accessed at en.wikipedia.org/wild/Reaction_rate on Dec. 18, 2011, 6 pages.
"Shear," Vocabulary.com, retrieved on Aug. 23, 2013, <URL: https://www.vocabulary.com/dictionary/shear>, 3 pages.
"Sheer," Vocabulary.com, retrieved on Aug. 23, 2013, <URL: https://www.vocabulary.com/dictionary/sheer>, 3 pages.
"View of NCT01171326 on Dec. 7, 2010," ClinicalTrials.gov archive, Dec. 7, 2010, retrieved on Sep. 9, 2013, <http://clinicaltrials.gov/archive/NCT01171326/2010_12_07>, 4 pages.
"View of NCT01362010 on Jun. 9, 2011," ClinicalTrials.gov archive, Jun. 9, 2011, retrieved on Sep. 9, 2013, < http://clinicaltrials.gov/archive/NCT01362010/2011_06_09>, 3 pages.
"What is TSC?," *Tuberous Sclerosis Alliance*, Jan. 1, 2005, retrieved on Feb. 6, 2014, <URL: http://www.tsalliance.org.pages. aspx?content=2>, 3 pages.
'Niram Chemicals' [online]. Niram Chemicals, [retrieved on Jul. 17, 2012]. Retrieved from the Internet: <URL: http://www.indiamart. com/niramchemicals/chemicals.html>, 7 pages.
'Surfactant' [online]. Wikipedia, 2010, [retrieved on Oct. 24, 2010]. Retrieved from the Internet: <URL: http://en.wikipedia.org/wiki/ Surfactant>, 7 pages.
Abrams et al., "Ciclopirox gel treatment of scalp seborrheic dermatitis," *Hydroxy-Piridones as Antifungal Agents with Special Emphasis on Onychomycosis*, 1999, Chapter 8, 45-50.
Adachi, Shuji. "Storage and Oxidative Stability of O/W/ Nanoemulsions." Foods Food Ingredients. J. Jpn. vol. 209, No. 11. 2004. 1 page.
Anton, N. et al. "Water-in-Oil Nano-Emulsion Formation by the phase inversion Temperature Method: A Novel and General Concept, a New Template for Nanoencapsulation," *Proceedings of the 33rd Annual Meeting and Exposition of the Controlled Release Society*, Jul. 2006, Vienna, Austria, 2 pages.
Arct et al., "Common Cosmetic Hydrophilic Ingredients as Penetration Modifiers of Flavonoids", International Journal of Cosmetic Science, 24(6):357-366 (2002)—Abstract, 1 page.
Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.
Austria, et al., "Stability of Vitamin C Derivatives in Solution and Topical Formulations", Journal of Pharmaceutical and Biomedical Analysis, 15:795-801 (1997).
Barry and Badal, "Stability of minocycline, doxycycline, and tetracycline stored in agar plates and microdilution trays," *Current Microbiology*, 1978, 1:33-36.
Bernstein, et al., Effects of the Immunomodulating Agent R837 on Acute and Latent Herpes Simplex Virus Type 2 Invections, Antimicrobial Agents and Chemotherapy, 33(9):1511-1515 (1989).
Blaney and Cook, "Topical use of tetracycline in the treatment of acne," *Arch Dermatol*, Jul. 1976, 112:971-973.
Blute, "Phase behavior of alkyl glycerol ether surfactants", Physical Chemistry Tenside Sur. Det., 35(3):207-212 (1998).
Brenes, et al., "Stability of Copigmented Anthocyanins and Asorbics Acid in a Grape Juice Model System", J. Agric Food Chem, 53(1):49-56 (2005)—Abstrace, 1 page.
Bronopol. Revtrieved online on Jun. 4, 2011. <URL:http:// chemicalland21.com/specialtychem/perchem/BRONOPOL.html>. Jul. 17, 2006. 4 pages.

(56) References Cited

OTHER PUBLICATIONS

Buck, et al., "Treatment of Vaginal Intraephithelial Neoplasia (Primarily Low Grade) with Imiquimod 5% Cream", Journal of Lower Genetial Tract Disease, 7(3):290-293 (2003).
Bunker,et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).
Burton, et al., "Hypertrichosis Due to Minoxidil", British Journal of Dermatology, 101:593-595 (1979).
Campos, et al., "Ascorbic Acid and Its Derivatives in Cosmetic Formulations", Cosmetics and Toiletries, 115(6):59-62 (2000)—Abstract, 1 page.
Carelli, et al., "Effect of Vehicles on Yohimbine Permeation Across Excised Hairless Mouse Skin", Pharm Acta Helv, 73(3):127-134 (1998)—Abstract, 1 page.
Cetearyl Alcohol, Natural Wellbeing, Copyrigh 2001-2012, retrieved on Apr. 10, 2014, http://www.naturalwellbeing.com/learning-center/Cetearyl_Alcohol, 3 pages.
Chebil, et al., "Soulbility of Flavonoids in Organic Solvents", J. Chem. Eng. Data, 52(5):1552-1556 (2007)—Abstract, 1 page.
Chevrant-Breton, et al., "Etude du Traitement Capillaire <<Bioscalin>> dans les Alopecies Diffuses de la Femme", Gazette Medicale, 93(17):75-79 (1986) [English abstract].
Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.
Chinnian, et al., "Photostability Profiles of Minoxidil Solutions", PDA J. Pharm Sci Technol., 50(2):94-98 (1996)—Abstract, 1 page.
Chollet, et al., "Development of a Topically Active Imiquimod Formulation", Pharmaceutical Development and Technology, 4(1):35-43 (1999).
Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.
Cloez-Tayarani. et al., "Differential effect of serotonin on cytokine production in lipopolysaccharide-stimulated human peripheral blood mononuclear cells: involvement of 5-hydroxytryptamine2A receptors," Int. Immunol., 2003, 15:233-40.
Colloidal Silica. Retrieved online on Jun. 4, 2011. <URL:http://www.grace.com/engineeredmaterials/materialsciences/colloidalsilica/default.aspx>. Copyright 2011. 4 pages.
Croda 2. Croda Cetomacrogol 1000 Product Information Sheet. 2011 (no month given). 1 page.
Croda. Aracel 165 Product Summary. 2011 (no month given). 1 page.
Cunha, "Minocycline versus Doxycycline in the treatment of Lyme Neuroborreliosis," Clin. Infect. Diseases, 2000, 30: 237-238.
Dawber, et al., "Hypertrichosis in Females Applying Minoxidil Topical Solution and in Normal Controls", JEADV, 17:271-275 (2003).
Dentinger, et al., "Stability of Nifedipine in an Extemporaneously Compounded Oral Solution", American Journal of Health-System Pharmacy, 60(10):1019-1022 (2003)—Abstract, 1 page.
Disorder. (2007). In the American Heritage Dictionary of the English Language. Retrieved from http://www.credoreference.com/entry/hmdictenglang/disorder. 1 page.
Draelos, Z. D. "Antiperspirants and the Hyperhidrosis Patients." Dermatologic Therapy. 2001. vol. 14. pp. 220-224.
Durian et al., "Scaling behavior in shaving cream," The Americal Physical Society, Dec. 1991, 44(12):R7902-7905.
Edens, et al., "Storage Stability and Safey of Active Vitamin C in a New Dual-Chamber Dispenser", Journal of Applied Cosmetology, 17(4):136-143 (1999)—Abstract, 1 page.
Edwards, "Imiquimod in Clinical Practice", J. Am Acad Dermatol., 43(1, Pt 2):S12-S17 (2000)—Abstract, 1 page.

Esposito, E. et al. "Nanosystems for Skin Hydration: A Comparative Study." International Journal of Cosmetic Science. 29. 2007. pp. 39-47.
Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.
Farahmand, et al., "Formulation and Evaluation of a Vitamin C Multiple Emulsion", Pharmaceutical Development and Technology, 11(2):255-261 (2006)—Abstract, 1 page.
Gelbard et al. "Primary Pediatric Hyperhidrosis: A Review of Current Treatment Options." Pediatric Dermatology. 2008. 25 (6). pp. 591-598.
Google search strategy for minocycline solubility, retrieved on Aug. 15, 2013, <http://www.googl.com/search?rls=com.microsoft%3Aen-us%3AIE-SearchBox&q-melocycline+solubility>, 1 page.
Harry, "Skin Penetration," The British Journal of Dermatology and Syphillis, 1941, 53:65-82.
Lee et al., "Historical review of melanoma treatment and outcomes," Clinics in Dermatology, 2013, 31: 141-147.
Livingstone and Hubel, "Segregation of form, color, movement, and depth: Anatomy, physiology, and perception," Science, May 1988, 240:740-749.
Merck Index, An Encyclopedia of Chemicals, Drugs, and Biologicals. 13th Edition. O'Neil et al eds. Entries 1058, 2350, 6143, and 8803. 2001. 7 pages.
*Molins PLC v. Textron Inc.*, 48 F.3d 1172, 33 USPQ2d 1823 (Fed. Cir. 1995), 19 pages.
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neves et al., "Rheological Properties of Vaginal Hydrophilic Polymer Gels," Current Drug Delivery, 2009, 6:83-92.
Prud'homme et al., Foams: theory, measurements and applications, Marcel Dekker, Inc., 1996, 327-328.
Purdy et al., "Transfusion-transmitted malaria: unpreventable by current donor exclusion guidelines?" Transfusion, Mar. 2004, 44:464.
Reregistration Eligibility Decision for Pyrethrins, EPA, Jun. 7, 2006, 108 pages.
Schmolka, "A review of block polymer surfactants," *Journal of the American Oil Chemists Society*, Mar. 1977, 54: 110-116.
Schott, "Rheology," *Remington's Pharmaceutical Sciences*, 17th Edition, 1985, 330-345.
Sciarra, "Aerosol Technology," *Kirk-Othmer Encyclopedia of Chemical Technology*, Jul. 2012, 20 pages.
Scully et al., "Cancers of the oral mucosa treatment and management," *Medscape Drugs, Diseases and Procedures*, Apr. 20, 2012, retrieved on Oct. 12, 2013, <http://emedicine.medscape.com/article/1075729-treatment>, 10 pages.
Sehgal, "Ciclopirox: a new topical pyrodonium antimycotic agent: A double-blind study in superficial dermatomycoses," *British Journal of Dermatology*, 1976, 95:83-88.
Softemul-165: Product Data Sheet, Mohini Organics PVT LTD, retrieved Apr. 10, 2014, http://www.mohiniorganics.com/Softemul165.html#, 1 page.
*Sun Pharmaceutical Industried Ltd. v. Eli Lilly and Co.*, 611 F.3d 1381, 95 USPQ2d 1797 (Fed. Cir. 2010),7 pages.
Tirmula et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.
Albrecht et al., "Topical minocycline foam for moderate to severe acne vulgaris: Phase 2 randomized double-blind, vehicle-controlled study results," J. Am. Acad. Dermatol., 2016, 74(6):1251-1252.
Chapter 1 Meaning of HLB Advantages and Limitations 1980; 4 pages.
Foamix Pharmaceuticals Statement: Use of Luviquat FC 370, Approved by Yohan Hazot, May 3, 2016, 3 pages.
Material Safety Data Sheet, Squalane, TCI America, 5 pages, https://www.spectrumchemical.com/MSDS/TC1-H0096.pdf. Published: Oct. 6, 2014.

(56) References Cited

OTHER PUBLICATIONS

Reply of the Patent Proprietor to the Notices of Opposition in European Application No. 03772600.7, dated May 9, 2016, 134 pages.
Sorbitan Esters, [online] retrieved on Jul. 1, 2016 from: http://www.drugfuture.com/chemdata/sorbitan-esters.html 2 pages.
Sreenivasan et al., "Studies on Castor Oil. I. Fatty Acid Composition of Castor Oil," Journal of the American Oil Chemists Society. 1956, 33:61-66.
Summons to Attend Oral Proceedings in European Application No. 03772600.7, dated Jun. 30, 2016, 19 pages.
Communication of a Notice of Opposition in European Application No. 03772600.7, dated Jan. 13, 2015, 36 pages.
Cremophor A Grades, BASF The Chemical Company, Jan. 2008, 6 pages.
Ellis et al., "The Treatment of Psoriasis with Liquor Carbonis Detergens," J. Invest Dermatology, 1948, 10:455-459.
Gels, UNC, The Pharmaceutics and Compounding Laboratory, retrieved on Aug. 25, 2014, http://pharmlabs.unc.edu/labs/gels/agents/htm, 4 pages.
Griffin, "Calculation of HLB Values of Non-Ionic Surfactants," Journal of the Society of Cosmetic Chemists, May 14, 1954, 249-256.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Luviquat Polymer Grades, BASF The Chemical Company, May 2012, 32 pages.
Material Safety Data Sheet, Luvitol EHO, Caelo, Nov. 28, 2013, 4 pages.
Material Safety Data Sheet, Liquor carbonis detergens, Caelo, Nov. 28, 2013, 5 pages.
Material Safety Data Sheet, Mineral Oil, Macron Fine Chemicals, Oct. 24, 2011, 6 pages.
Oh et al., "Antimicrobial activity of ethanol, glycerol monolaurate or lactic acid against Listeria moncylogenes,"Int. J. Food Microbiology, 1993, 20:239-246.
Omega-9 Fatty Acids (Oleic Acid), Orthomolecular.org, Dec. 2004, retrieved on Aug. 15, 2014, http://orthomolecular.org/nutrients/omega9.html. 1 page.
Refina, "Viscosity Guide for Paints, Petroleum & Food Products," accessed Mar. 4, 2015, http://www.refina.co.uk/webpdfs/info_docs/Viscosity_guide_chart.pdf, 2 pages.
Rohstoffinformationen, Hoffmann Mineral, 2008, 8 pages (with English translation).
Thorgeirsdottir et al., "Antimicrobial activity of monocaprin: a monoglyceride with potential use as a denture disinfectant," Acta Odontologica Scandinavica, Feb. 2006, 64:21-26 (Abstract only).
Ziolkowsky, "Moderne Aerosolschaume in der Kosmetik (Modern Aerosol Foams in Chemical and Marketing Aspects),", Seifen-Ole-Fette-Wachse, Aug. 1986, 112(13): 427-429 (with English translation).
Al-Mughrabi et al., "Effectiveness of Essential Oils and Their Combinations with Aluminum Starch Octenylsuccinate on Potato Storage Pathogens," TEOP, 2013, 16(1):23-31.
Beauty Banter, "Interesting list of comedogenic ingredients!!!!!!!!!!!!" QVC blog, Interesting list of comedogenic ingredients, 2014, 1-14.
Chemical Characteristics, The Olive Oil Source, © 1998-2015, retrieved on Jun. 12, 2015, http://www.oliveoilsource.com/page/chemical-characteristics, 10 pages.
Codex Standard for Olive Oils and Olive Pomace Oils Codex Stan 33-1981, Adopted in 1981, recently amended 2013, 8 pages.
Devos and Miller, "Antisense Oligonucleotides: Treating neurodegeneration at the Level of RNA," Neurotherapeutics, 2013, 10:486-497.
Haw, "The HLB System: A Time Saving Guide to Surfactant Selection," Presentation to the Midwest Chapter of the Society of Cosmetic Chemists, Mar. 9, 2004, 39 pages.

Mailer, "Chemistry and quality of olive oil," NSW Dept. of Primary Industries, Aug. 2006, Primefact 227, 1-4.
Permethrin (Insecticide), Wildpro, retrieved on Jun. 4, 2015, http://wildpro.twycrosszoo.org/S/00Chem/ChComplex/perm.htm, 5 pages.
United States Standards for Grades of Olive Oil and Olive-Pomace Oil, United States Dept. of Agriculture, Oct. 25, 2010, 21 pages.
WebMD, "Psoriasis Health Center," 2014, retrieved Apr. 13, 2015, http://www.webmd.com/skin-problems-and-treatments/psoriasis/psoriasis-symptoms, 3 pages.
WebMD, "Understanding Rosacea—the Basics," 2014, retrieved Apr. 13, 2015, http://www.webmd.com/skin-problems-and-treatments/understanding-rosacea-basics, 5 pages.
Williams et al., "Acne vulgaris," Lancet, 2012, 379:361-372.
Material Safety Data Sheet, Butane, Gas Innovations, Sep. 7, 2007, 3 pages.
Material Safety Data Sheet, Carbon Dioxide, Airgas, Feb. 11, 2016, 11 pages.
Material Safety Data Sheet, Dimethyl Ether, Airgas, May 14, 2015, 12 pages.
Material Safety Data Sheet, N-Butane, Airgas, May 7, 2015, 13 pages.
Material Safety Data Sheet, Nitrous Oxide, Airgas, Feb. 11, 2016, 11 pages.
Material Safety Data Sheet, Propane, Airgas, Oct. 20, 2015, 12 pages.
Sanders et al., "Stabilization of Aerosol Emulsions and Foams," J. Soc. Cosmet. Chem., 1970, 21:377-391.
Allantoin, Römpp Online, retrieved on Sep. 23, 2015, https://roempp.thieme.de/roempp4.0/do/data/RD-O 1-01552, 5 pages.
Coconut Oil, Wikipedia, the free encyclopedia, retrieved on Jul. 3, 2015, https://en.wikipedia.org/wiki/Coconut_oil, 8 pages.
Communication of a Notice of Opposition in European Application No. 03772600.7, dated Sep. 23, 2015, 42 pages.
Communication of a Notice of Opposition in European Application No. 03772600.7, dated Sep. 24, 2015, 30 pages.
Diethyltoluamid, Wikipedia, the free encyclopedia, retrieved on Sep. 11, 2015, https://de.wikipedia.org/wiki/Diethyltoluamid, 12 pages.
Dimethylphthalate, Wikipedia, the free encyclopedia, retrieved on Sep. 11, 2015, http://de.wikipedia.org/wiki/Dimethylphthalat, 8 pages.
Everything but the Olive, (the Olive Oil Source 1998-2016). http://www.oliveoilsource.com/pageAchemical-characteristics).
Healy, "Gelled Emollient Systems for Controlled Fragrance Release and Enhanced Product Performance," Cosmetics and toiletries, 2002, 117(2): 47-54.
Kaur et al., "Formulation Development of Self Nanoemulsifying Drug Delivery System (SNEDDS) of Celecoxib for Improvement of Oral Bioavailability," Pharmacophore, 2013, 4(4):120-133.
Lamisil, Lamisil.http://www.fda.gov/downloads/Drugs/DrugSafety/PostmarketDrugSafetyInformationforPatientsandProviders/ucm052213.pdf, Published: Apr. 2001.
Leunapon-F, LEUNA-Tenside, Screenshot, retrieved on Sep. 18, 2015, http://www.leuna-tenside.de/2006_7_14_3143/2006_8_7_5750/2006_8_7 241/cas-68439-49-6, 1 page.
Mead, "Electrostatic Mechanisms Underlie Neomycin Block of the Cardiac Ryanodine Receptor Channel (RyR2)," Biophysical Journal, 2004, (87): 3814-3825.
Rowe et al., "Glyceryl Monooleate," Handbook of Pharmaceutical Excipients, 2011, pp. 1-5, retrieved on Dec. 19, 2011, http://www.medicinescomplete.com/mc/excipients/current/1001938996.htm?q=glyceryl%20monooleate&t=search&ss=text&p=1# hit.
Rowe et al., "Octyldodecanol," Handbook of Pharmaceutical Excipients, 2011, pp. 1-4, retrieved on Dec. 19, 2011, URL:http://www.medicinescomplete.com/mc/excipients/current/1001942450.htm?q=octyldodecanol&t=search&ss=text&p=1# hit.
Rowe et al., "Sucrose Palmitate," Handbook of Pharmaceutical Excipients, 2011, pp. 1-5, retrieved on Dec. 19, 2011, URL:http://www.medicinescomplete.com/mc/excipients/current/EXP-TD-c46-mn0001.htm?q=sucrose%20stearate&t=search&ss=text&p=1# hit.

(56) References Cited

OTHER PUBLICATIONS

Rowe et al., "Sucrose Stearate," Handbook of Pharmaceutical Excipients, 2011, pp. 1-4, retrieved on Dec. 19, 2011, URL:http://www.medicinescomplete.com/mc/excipients/current/EXP-TD-cll-mnOOO1-mnOOO1.htm?q=sucrose%20stearate&t=search&ss=text&p=3# hit.
RSES (Oil in Refrigerator Systems, Service Application Manual, 2009).
Security Datasheet, Luvitol EHO, Cetearyloctanoat, Nov. 27, 2013, 10 pages.
Sigma-Aldrich. http://www.sigmaaldrich.com/catalog/product/sial/p1754?lang=en® ion=. Published:Mar. 5, 2014.
Suppositories?, CareCure, http://sci.rutgers.edu/forum/showthread.php?4176-Suppositories. Published: Apr. 16, 2002.
Triethanolamine, haute.de, retrieved on Sep. 14, 2015, http://www.haut.de/service/inci/anzeige&id=16384&query=Triethanolamine&funktio . . . , 3 pages.
Valenta, "Effects of Penetration Enhancers on the In-vitro Percutaneous Absorption of Progesterone," J. Phann. Pharrnacol., 1997, 49: 955-959.
Wenninger et al., "International Cosmetic Ingredient Dictionary and Handbook," The Cosmetic, Toiletry, and Fragrance Association, Washington, DC., 1997, vol. 1, 4 pages.
Williams et al., "Urea analogues in propylene glycol as penetration enhancers in human skin," International Journal of Pharmaceutics, 1989, 36, 43-50.
Wu et al., "Interaction of Fatty Acid Monolayers with Cobalt Nanoparticles," Nano Letters, 2004, 4(2): 383-386.
Alcohol, Wikipedia, the free encyclopedia, retrieved on May 17, 2014, http://en.wikipedia.org/wiki/Alcohol, 17 pages.
Clobetasol Propionate Cream and Ointment, Apr. 2006, retrieved Jul. 3, 2014, http://dailymed.nlm.nih.gov/dailymed/archives/fdaDrugInfo.cfm?archiveid=994, 7 pages.
Cole and Gazewood, "Diagnosis and Treatment of Impetigo," American Family Physicial Website, 2007, http://www.aafp.org/afp, 6 pages.
Le Vine et al., "Components of the Goeckerman Regimen," Journal of Investigative Dermatology, 1979, 73:170-173.
Oranje et al., "Topical retapamulin ointment, 1%, versus sodium fusidate ointment, 2%, for impetigo: a randomized, observer-blinded, noninferiority study," Dermatology, 2007, 215(4):331-340.
Polystyrene, Wikipedia the free encyclopedia, retrieved Apr. 21, 2014, http://web.archive.org/web/20060312210423/http://en.wikipedia.org/wiki/Polystyrene, 4 pages.
Vera et al., "Scattering optics of Foam," Applied Optics, Aug. 20, 2001, 40(24):4210-4214.

* cited by examiner

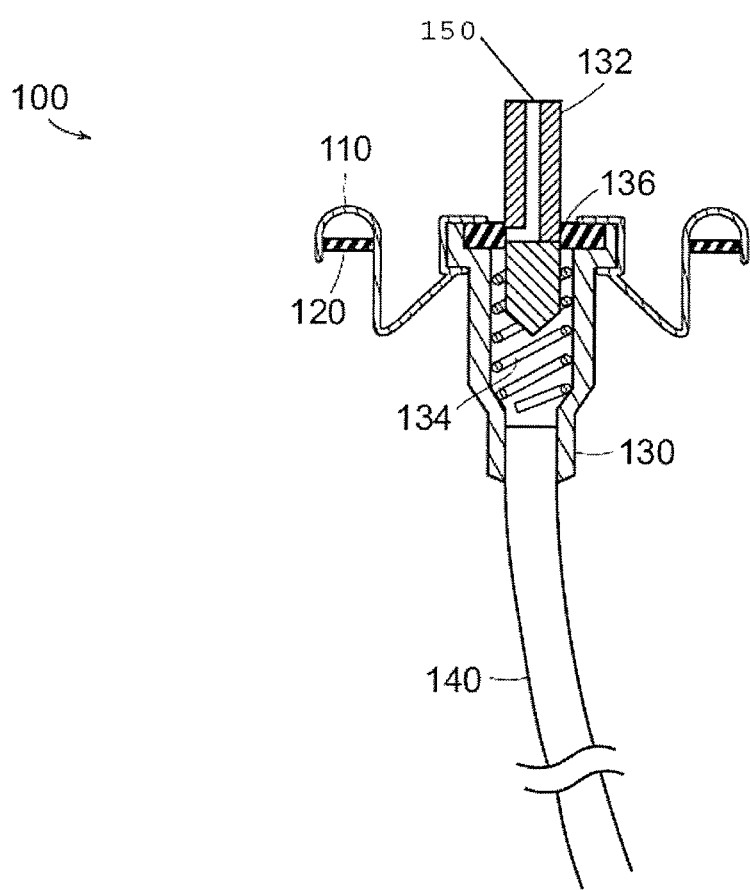

NONSTEROIDAL IMMUNOMODULATING KIT AND COMPOSITION AND USES THEREOF

CROSS REFERENCE TO RELATED APPLICATIONS

This application is a continuation-in-part application of co-pending International Patent Application No. IB03/005527 designating the United States and filed on Oct. 24, 2003, which claims the benefit of priority under 35 U.S.C. §119(e) to U.S. Patent Application Ser. No. 60/429,546, filed on Nov. 29, 2002, both entitled "Cosmetic and Pharmaceutical Foam," and which also claims the benefit of priority under 35 USC§119(a) to Israeli Patent Appl. No. 152486, filed Oct. 25, 2002, all of which are hereby incorporated in their entirety by reference.

This application is a continuation-in-part application of co-pending U.S. patent application Ser. No. 10/911,367, filed on Aug. 4, 2004, which claims the benefit of priority under 35 U.S.C. §119(e) to U.S. Patent Application Ser. No. 60/492,385, filed on Aug. 4, 2003, both entitled "Foam Carrier Containing Amphiphilic Copolymer Gelling Agent" and both hereby incorporated in their entirety by reference.

BACKGROUND OF THE INVENTION

Nonsteroidal immunomodulating agents have been used to relieve inflammation and mild to moderate pain; they are also used for fever and inflammation. Such drugs are usually administered systemically and most often by oral administration. The most common side effect occurring during therapy with certain immunomodulating agents are gastrointestinal disturbances.

Certain nonsteroidal immunomodulating agents are also available in topical dosage form. Compositions containing nonsteroidal immunomodulating agents for topical treatment of dermatologic and gynecological disorders are available in cream, lotion gel and ointment forms. While semisolid compositions, such as creams, lotions, gels and ointments are commonly used by consumers, new forms are desirable, in order to achieve better control of the application, while maintaining or bestowing the skin beneficial properties of such products. Thus, the development of new compositions, having breakable foam consistency when released from a container and liquid properties when applied onto the skin is advantageous.

Foams and, in particular, foam emulsions are complicated systems which do not form under all circumstances. Slight shifts in foam emulsion composition, such as by the addition of active ingredients, may destabilize the foam.

There have been a few attempts to create foams including anti-inflammatory agents. U.S. Pat. No. 6,126,920 discloses treatment of various skin diseases, and in particular, scalp psoriasis, using a foamable pharmaceutical composition containing a corticosteroid active substance, an aliphatic alcohol, water, a fatty alcohol, a surface-active agent, a propellant and a buffering agent. The foamable composition contains 40-90% composition of an aliphatic alcohol. Alcohols, and in particular the methyl, ethyl and isopropyl alcohols which are preferred in U.S. Pat. No. 6,126,920, are defatting and irritating agents and may cause skin to become dry and cracked. EP 0535327 B1 discloses a pharmaceutical composition containing (a) 4-biphenylacetic acid (Felbinac); and (b) a carrier which comprises water, ethanol, an aerosol propellant and an ethoxylated stearyl alcohol surfactant. The carrier is adapted to create a quick-break foam. EP 0 270 316 (A3) Patent describes topical compositions including 1-substituted imidazole and non-steroidal anti-inflammatory drugs for treatment of acne. U.S. Pat. No. 6,358,541 teaches preparations for the treatment of androgenetic alopecia comprise saw palmetto berry extract containing phytosterols and one or more low irritability constituents that enhance penetration of the extract into hair follicular pores, e.g., adapalene, tretinoin, retinaldehyde, tazarotene, salicylic acid, azelaic acid, and glycolic acid, wherein the preparation further contains a topical vehicle selected from the group consisting of liquid, gel, foam, styling mousse, styling hair tonic and styling hair spray. U.S. Pat. No. 5,171,577 relates to a process for the preparation of cosmetics or pharmaceutical foam by foaming with the aid of a propellant, the cosmetic or pharmaceutical product includes a dispersion of a water-immiscible phase dispersed in an aqueous medium stabilized with niosomes including one or more layers of a nonionic lipid compound encapsulating an aqueous phase. In certain embodiments, the product may contain at least one product selected from the group consisting of a vitamin, a hormone, an enzyme, a vaccine, an anti-inflammatory agent, an antibiotic, a bactericide, an antifungal agent, an agent to prevent hair loss, an agent to promote hair growth and additional active agents. U.S. Pat. No. 4,981,677 teaches a skin conditioning composition for application to the skin including an oil-in-water emulsion and a propellant including at least 10 percent by weight of petrolatum, at least 50 weight percent of water, an emulsifier having a hydrophilic-lipophilic Balance value of 6 to 10 and a starch or modified starch ester. U.S. Pat. No. 5,002,680 describes a mild skin-cleansing aerosol mousse-forming emulsion including a mild nonsoap anionic or amphoteric surfactant; a polymeric skin feel aid, a moisturizer (preferably glycerin); water; and a propellant. WO 00/15193 teaches a pharmaceutical foam composition including (a) an active ingredient; (b) an occlusive agent; (c) an aqueous solvent; and (d) an organic cosolvent; wherein the active ingredient is insoluble in water and insoluble in both water and the occlusive agent; and wherein there is enough occlusive agent to form an occlusive layer on the skin.

SUMMARY OF THE INVENTION present invention provides a therapeutic kit for providing a safe and effective dosage of a nonsteroidal immunomodulating agent, including an aerosol packaging assembly including: a container accommodating a pressurized product, and an outlet capable of releasing the pressurized product as a foam, wherein the pressurized product includes a foamable composition including: a nonsteroidal immunomodulating agent, at least one organic carrier selected from the group consisting of a hydrophobic organic carrier, a polar solvent, an emollient and mixtures thereof, at a concentration of about 2% to about 50% by weight, a surface-active agent, about 0.01% to about 5% by weight of at least one polymeric additive selected from the group consisting of a bio-adhesive agent, a gelling agent, a film forming agent and a phase change agent, water, and liquefied or compressed gas propellant at a concentration of about 3% to about 25% by weight of the total composition.

According to further embodiments of the present invention the foamable composition is an emulsion.

According to still further embodiments of the present invention the foamable composition is selected from the group consisting of an oil-in-water emulsion and a water in oil emulsion.

According to still further embodiments of the present invention the foamable composition is substantially alcohol-free.

Preferably, the composition of the present invention further comprises a therapeutically active foam adjuvant is selected from the group consisting of a fatty alcohol having 15 or more carbons in their carbon chain, a fatty acid having 16 or more carbons in their carbon chain, a fatty alcohols, derived from beeswax and including a mixture of alcohols, a majority of which has at least 20 carbon atoms in their carbon chain, a fatty alcohol having at least one double bond, a fatty acid having at least one double bond, a branched fatty alcohol, a branched fatty acid, a fatty acid substituted with a hydroxyl group, cetyl alcohol, stearyl alcohol, arachidyl alcohol, behenyl alcohol, 1-triacontanol, hexadecanoic acid, stearic acid, arachidic acid, behenic acid, octacosanoic acid, 12-hydroxy stearic acid and mixtures thereof. The concentration of the therapeutically active foam adjuvant is in the range of about 0.1% to about 5% by weight.

According to further embodiments of the present invention the foamable composition further includes a second therapeutic agent selected from the group consisting of an anti-infective, an antibiotic, an antibacterial agent, an antifungal agent, an antiviral agent, an antiparasitic agent, an steroidal antiinflammatory agent, an immunosuppressive agent, an immunomodulator, an immunoregulating agent, a hormonal agent, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, a NSAID, an antiproliferative agent, an anticancer agent, a photodynamic therapy agent, benzoyl chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, talc, carbon, an anti wrinkle agent, a skin whitening agent, a skin protective agent, a masking agent, an anti-wart agent, a refatting agent, a lubricating agent and mixtures thereof.

According to a second embodiment of the present invention there is provided a therapeutic foamable composition including: a nonsteroidal immunomodulating agent, a therapeutically active oil agent, a surface-active agent, a therapeutically active foam adjuvant, selected from the group consisting of a fatty alcohol, a fatty acid, a hydroxyl fatty acid, and mixtures thereof, about 0.01% to about 5% by weight of at least one polymeric additive selected from the group consisting of a bioadhesive agent, a gelling agent, a film forming agent and a phase change agent, water, and liquefied or compressed gas propellant at a concentration of about 3% to about 25% by weight of the total composition.

According to further embodiments of the present invention the foamable composition further includes a second therapeutic agent.

According to further embodiments of the present invention the composition does not contain petrolatum.

According to the present invention there is provided a method of producing a therapeutic kit, including a nonsteroidal immunomodulating agent, including: providing a foamable therapeutic composition including: a nonsteroidal immunomodulating agent at a therapeutically effective concentration, at least one organic carrier selected from a hydrophobic organic carrier, a polar solvent, an emollient and mixtures thereof, at a concentration of about 2% to about 50% by weight, a surface-active agent, about 0.01% to about 5% by weight of a polymeric additive selected from a bioadhesive agent, a gelling agent, a film forming agent and a phase change agent, and water, introducing the foamable composition in an aerosol packaging assembly, consisting of a container, suitable for containing a pressurized product and a valve, capable of extruding a foam, and introducing to the aerosol packaging assembly a liquefied or compressed gas propellant at a concentration of about 3% to about 25% by weight of the total composition.

According to the present invention there is also provided a method of treating, alleviating or preventing a disorders of the skin, a body cavity or mucosal surface, wherein the disorder involves inflammation as one of its etiological factors, including: administering topically to a subject having the disorder, a foamed composition including: a nonsteroidal immunomodulating agent, at least one organic carrier selected from a hydrophobic organic carrier, a polar solvent, an emollient and mixtures thereof, at a concentration of about 2% to about 50% by weight, about 0.1% to about 5% by weight of a surface-active agent, about 0.01% to about 5% by weight of a polymeric additive selected from a bioadhesive agent, a gelling agent, a film forming agent and a phase change agent, and water, wherein the nonsteroidal immunomodulating agent is administered in a therapeutically effective amount.

According to still further embodiments of the methods according to the present invention the disorder is selected from the group consisting of a dermatose, a dermatitis, a vaginal disorder, a vulvar disorder, an anal disorder, a disorder of a body cavity, an ear disorder, a disorder of the nose, a disorder of the respiratory system, a bacterial infection, fungal infection, viral infection, dermatosis, dermatitis, parasitic infections, disorders of hair follicles and sebaceous glands, scaling papular diseases, benign tumors, malignant tumors, reactions to sunlight, bullous diseases, pigmentation disorders, disorders of cornification, pressure sores, disorders of sweating, inflammatory reactions, xerosis, ichthyosis, allergy, burn, wound, cut, chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, osteoarthritis, joint pain, hormonal disorder, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum, and wherein the disorder is responsive to treatment with the nonsteroidal immunomodulating agent.

BRIEF DESCRIPTION OF THE DRAWING

The invention is described with reference to the FIGURE which is presented for the purpose of illustration and are not intended to be limiting of the invention.

The FIGURE is a schematic illustration of an aerosol valve suitable for use in the aerosol packaging assembly according to in one or more embodiments of the invention.

DETAILED DESCRIPTION OF THE INVENTION

The present invention provides a therapeutic kit including a nonsteroidal immunomodulating agent (also termed herein "nonsteroidal anti-inflammatory agent" and "NSAID"). The kit includes an aerosol packaging assembly having a container accommodating a pressurized product and an outlet capable of releasing the pressurized product as a foam.

Aerosol Packaging Assembly

The aerosol packaging assembly typically includes a container suitable for accommodating a pressurized product and an outlet capable of releasing a foam. The outlet is typically a valve. The FIGURE illustrates a typical aerosol valve 100. The valve is made up of the valve cup 110 typically constructed from tinplated steel, or aluminum, an outer gasket 120, which is the seal between the valve cup and the aerosol can (not shown), a valve housing 130, which contains the valve stem 132, spring 134 and inner gasket 136, and a dip tube 140, which allows the liquid to enter valve. The valve stem is the tap through which the product flows. The inner gasket 136 covers the aperture 150 (hole) in the valve stem. The valve spring 134 is usually made of stainless steel.

The valve stem is fitted with small apertures 150 (also termed "orifices" and "holes"), through which the product flows. Valves may contain one, two, three, four or more apertures, depending on the nature of the product to be dispensed. In the closed position, the aperture(s) is covered by the inner gasket. When the actuator is depressed it pushes the valve stem through the inner gasket, and the aperture(s) is uncovered, allowing liquid to pass through the valve and into the actuator.

The valve can have a stem with 1 to 4 apertures, or 1 to 2 apertures. Each aperture can have a diameter of about 0.2 mm to about 1 mm, or a diameter of about 0.3 mm to about 0.8 mm. The total aperture area, i.e., the sum of areas of all apertures in a given stem, is between about 0.01 mm$^2$ and 1 mm$^2$ or the total aperture area is between about 0.04 mm$^2$ and 0.5 mm$^2$.

Pharmaceutical Composition

All % values are provided on a weight (w/w) basis.

According to one or more embodiments of the present invention, the foamable therapeutic composition for administration to the skin, a body surface, a body cavity or mucosal surface, e.g., the mucosa of the nose, mouth, eye, ear, respiratory system, vagina or rectum (severally and interchangeably termed herein "target site") includes:

(1) a nonsteroidal immunomodulating agent, wherein the amount of the nonsteroidal immunomodulating agent is effective in the treatment of a disorder of the target site;

(2) at least one organic carrier selected from a hydrophobic organic carrier, a polar solvent, an emollient and mixtures thereof, at a concentration of about 2% to about 5%, or about 5% to about 10%; or about 10% to about 20%; or about 20% to about 50% by weight;

(3) about 0.1% to about 5% by weight of a surface-active agent;

(4) about 0.01% to about 5% by weight of at least one polymeric agent selected from a bioadhesive agent, a gelling agent, a film forming agent and a phase change agent; and (5) a liquefied or compressed gas propellant at a concentration of about 3% to about 25% by weight of the total composition.

Water and optional ingredients are added to complete the total mass to 100%. Upon release from an aerosol container, the foamable composition forms an expanded foam suitable for topical administration.

According to one or more embodiments, the foamable composition is substantially alcohol-free, i.e., free of short chain alcohols. Short chain alcohols, having up to 5 carbon atoms in their carbon chain skeleton and one hydroxyl group, such as ethanol, propanol, isopropanol, butanol, iso-butanol, t-butanol and pentanol, are considered less desirable solvents or polar solvents due to their skin-irritating effect. Thus, the composition is substantially alcohol-free and includes less than about 5% final concentration of lower alcohols, preferably less than about 2%, more preferably less than about 1%.

In one or more embodiments, at least a portion of the NSAID is suspended in the composition, yet, in other embodiments, the NSAID is dissolved in the composition.

In one or more embodiments, the foam composition is formulated as an oil-in-water emulsion or oil-in-water microemulsion.

In one or more embodiments, the concentration of surface-active agent about 0.1% to about 5%, or from about 0.2% to about 2%.

Inflammation is defined as "redness, swelling, and fever in a local area of the body, often with pain and disturbed function, in reaction to an infection or to a physical or chemical injury" (Random House Webster's Dictionary). Typical symptoms of disorders of the skin, body surfaces, body cavities and mucosal surfaces (e.g., the mucosa of the nose, mouth, eye, ear, respiratory system, vagina or rectum) that involve inflammation, as at least one of their etiological factors, include redness (rash, erythema), tissue thickening and/or swelling (oedema), itch (pruritus), blistering and exudate. Inflammatory disorders can by short term or long term (chronic). Inflammation typically involves overproduction of pro-inflammatory cytokines, such as TNF-alpha, TNF-beta, interleukin-1, interleukin-4, interleukin-6, interleukin-10, interleukin-12, IFN-gamma from T cells, or increased release of cytokines and pro-inflammatory mediators from mast cells.

In the context of the present invention, a nonsteroidal immunomodulating agent (also termed herein "nonsteroidal anti-inflammatory agent" and "NSAID") is a pharmaceutically active compound, other than a corticosteroid, which affects the immune system in a fashion that results in a reduction, inhibition, prevention, amelioration or prevention of an inflammatory process and/or the symptoms of inflammation and or the production pro-inflammatory cytokines and other pro-inflammatory mediators, thereby treating or preventing a disease that involves inflammation.

In one or more embodiments, the NSAID is an inhibitor of the cyclooxygenase (COX) enzyme. Two forms of cyclooxygenase are known today: the constitutive cyclooxygenase (COX-1); and the inducible cyclooxygenase (COX-2), which is proinflammatory. Thus, in one or more embodiments of the present invention, the NSAID is selected from the group consisting of a COX-1 inhibitor, a COX-2 inhibitor or a non-selective NSAID, which simultaneously inhibits both COX-1 and COX-2.

In one or more embodiments, the NSAID is salicylic acid a salicylic acid derivatives. Exemplary salicylic acid derivative include, in a non limiting fashion, aspirin, sodium salicylate, choline magnesium trislicylate, salsalate, diflunisal, salicylsalicylic acid, sulfasalazine, olsalazine, esters of salicylic acid with a carboxylic acid, esters of salicylic acid with a dicarboxylic acid, esters of salicylic acid with a fatty acid, esters of salicylic acid with a hydroxyl fatty acid, esters of salicylic acid with an essential fatty acid, esters of salicylic acid with a polycarboxylic acid, and any compound wherein salicylic acid is linked to an organic moiety through a covalent bond.

In one or more embodiments, the NSAID is encapsulated in particles, microparticles, nanoparticles, microcapsules, microsphres, nanocapsules, nanospheres, liposomes, niosomes, polymer matrix, nanocrystals or microsponges.

In one or more embodiments, the NSAID is para-aminophenol (e.g., acetaminophen) and salts and derivatives thereof.

In one or more embodiments, the NSAID is an indole or an indole-acetic acid derivative (e.g., indomethacin, sulindac, etodolac) and salts and derivatives thereof.

In one or more embodiments, the NSAID is an aryl acetic acids (e.g., tolmetin, diclofenac, ketorolac) and salts and derivatives thereof.

In one or more embodiments, the NSAID is an arylpropionic acid and salts and derivatives thereof. Exemplary arylpropionic acid derivative include, in a non limiting fashion, are ibuprofen, naproxen, flubiprofen, ketoprofen, fenoprofen, oxaprozin.

In one or more embodiments, the NSAID is anthranilic acids or an anthranilic acid derivative, also termed "fenamates" (e.g., mefenamic acid, meclofenamic acid) and salts and derivatives thereof.

In one or more embodiments, the NSAID is selected from the group of enolic acids, enolic acid salts, enolic acid esters, amides, anhydrides and salts and derivatives thereof. Non-limiting examples of enolic acid derivatives include oxicams (piroxicam, tenoxicam) and pyrazolidinediones (phenylbutazone, oxyphenthratrazone)

Yet, in additional embodiments, the NSAID is an alkanone (e.g., nabumetone).

Selective COX-2 Inhibitors include, in an exemplary manner diaryl-substituted furanones (e.g., Rofecoxib); diaryl-substituted pyrazoles (e.g., Celecoxib); indole acetic acids (e.g., Etodolac); and sulfonanilides (e.g., Nimesulide) and salts and derivatives thereof.

Certain imidazole drugs (e.g., ketoconazole) also possess anti-inflammatory properties, (See: J Am Acad. Dermatol. 1991 August; 25(2 Pt 1):257-61).

Another group of nonsteroidal immunomodulating agents includes agents, which inhibit pro-inflammatory cytokines, such as TNF-alpha, TNF-beta, interleukin-1, interleukin-4, interleukin-6, interleukin-10, interleukin-12 and IFN-gamma from T cells, which are especially important in the induction of inflammation or inhibit the release of cytokines and pro-inflammatory mediators from mast cells.

Agents that are used to affect the untoward influence of pro-inflammatory cytokines are chemically or biologically-originated materials that suppress the pro-inflammatory effect of a pro-inflammatory cytokine via various mechanisms, including, but not limited to (a) inhibiting the formation of a pro-inflammatory cytokine; (b) suppressing the interaction of a pro-inflammatory cytokine with its receptors; or (c) neutralization the proinflammatory cytokine by direct or indirect interaction.

Examples of chemical anti TNF-α agents are known pharmaceutical materials, such as pentoxifylline, propentofylline, torbafylline (and other related xanthines), amiloride, chloroquine, thalidomide and structural analogs thereof. Examples for biological anti-TNF-α agents are anti-TNF-α antibodies and soluble TNF-α receptors. Additional compounds are those that impair the signal transduction cascade from the receptor to other functional organs of the living cell. Such active agents, as well additional compounds, which are capable of inhibiting the production or otherwise suppressing the pro-inflammatory effects of TNF-α can be used in the composition of the present invention.

Immunosuppressant agents, immunoregulating agents and immunomodulators constitute an additional class of nonsteroidal anti-inflammatory agents, which are used according to the present invention. Such agents are chemically or biologically-derived agents that modify the immune response or the functioning of the immune system (as by the stimulation of antibody formation or the inhibition of white blood cell activity). Immunosuppressant agents and immunomodulators include, among other options, cyclic peptides, such as cyclosporine, tacrolimus, tresperimus, pimecrolimus, sirolimus (rapamycin), verolimus, laflunimus, laquinimod and imiquimod. In one or more embodiments, the non steroidal immunomodulating agent is a calcineurin Inhibitor.

In one or more embodiments, the NSAID is a nitric oxide inhibitor. Nitric oxide (NO) is a potent secondary messenger that is both highly reactive and highly diffusible. It is generated physiologically by a family of enzymes, referred to as NO synthases (NOS). Overproduction of NO plays a key role in the pathology of a wide range of disorders including disorders that involve inflammation, and NOS inhibitors have been suggested as anti-inflammatory agents. Agents that neutralize NO (also called "NO scavengers") are considered as potential anti-inflammatory agents as well.

Also useful are compounds that inhibit or slow down the migration of leucocytes (white blood cell), e.g., macrophages, neutrophils, and monocytes towards an afflicted skin surface or mucosal membrane, which is known to accelerate the inflammatory process.

Among other inhibitors of leucocyte chemoaxis, dicarboxylic acids, having between about 6 and about 14 carbon atoms in their carbon atom skeleton are particularly useful in the treatment of disorders of the skin and mucosal membranes that involve inflammation. Suitable dicarboxylic acid moieties include, but are not limited to, adipic acid, pimelic acid, suberic acid, azelaic acid, sebacic acid, 1,11-undecanedioic acid, 1,12-dodecanedioic acid, 1,13-tridecanedioic acid and 1,14-tetradecanedioic acid. Thus, in one or more embodiments of the present invention, dicarboxylic acids, having between about 6 and about 14 carbon atoms in their carbon atom skeleton, as well as their salts and derivatives (e.g., esters, amides, mercapto-derivatives, anhydraides), are useful immunomodulators in the treatment of disorders of the skin and mucosal membranes that involve inflammation. Azelaic acid and its salts and derivatives are preferred.

Certain preferred dicarboxylic acid derivatives include a dicarboxylic acid wherein at least one ester moiety of the compound comprises a keratolytic agent, selected from the group consisting of alpha-hydroxy acids and derivatives thereof, beta-hydroxy acids and derivatives thereof, hydroxybenzoic acid and their ester, anhydride and amine derivatives, alkylhydroxybenzoate, dihydroxy benzene and their ester, anhydride and amide derivatives, cresols and their ester, anhydride and amide derivatives. Keratolytic agents also include alcohol derivatives of Vitamin A (retinoic acid), e.g., retinol and derivatives thereof, as provided in U.S. Pat. No. 6,180,669. Additional preferred dicarboxylic acid derivatives comprise at least one ester of a active alcohol moiety, selected from the groups of steroid hormones, corticosteroids, vitamin E and vitamin D, as provided in U.S. patent application 20040191196.

Mixtures of these non-steroidal immunomodulators may also be employed according to the present invention.

Solubility of the nonsteroidal immunmodulating agent is an important factor in the development of a stable foamable composition according to the present invention. Thus, in one or more embodiments, the nonsteroidal immunmodulating agent is soluble in the aqueous phase of the emulsion; in other embodiments, wherein the agent possesses hydrophobic characteristics the agent is soluble in the oil phase of the emulsion. Yet, in additional embodiments, the nonsteroidal immunmodulating agent is difficult to solubilize in either the aqueous phase of the water phase and thus, it is suspended in the emulsion, which contains suspension-stabilizing agents, i.e., the polymeric agents that are listed herein. Thus, in certain embodiments of the present invention, the composition and properties of the aqueous phase of the emulsion (e.g., pH, electrolyte concentration and chelating agents) and/or the composition of the oil phase of the emulsion are adjusted to attain a desirable solubility profile of the active agent.

The NSAID is included in the composition of the present invention in a concentration that provides a desirable ratio between the efficacy and safety. Typically, NSAIDs are included in the composition in a concentration between about 0.05% and about 24%. However, in some embodiments, the concentration of between about 0.05% and about 2%, in other embodiment between about 2% and about 5%, and in additional embodiments between about 5% and about 12% or between about 12% and about 24%.

In one or more embodiments, the NSAID is a COX-1 inhibitor, at a concentration between about 0.05% and about 6%.

In one or more embodiments, the NSAID is a COX-2 inhibitor, at a concentration between about 0.05% and about 6%.

In one or more embodiments, the NSAID is diclofenac, at a concentration between about 0.05% and about 4%.

In one or more embodiments, the NSAID is piroxicam, at a concentration between about 0.05% and about 4%.

In one or more embodiments, the NSAID is selected from the group consisting of cyclosporine, tacrolimus, tresperimus, pimecrolimus, sirolimus (rapamycin), verolimus, laflunimus, laquinimod and imiquimod, at a concentration between about 0.05% and about 4%.

In one or more embodiments, the NSAID is a calcineurin Inhibitor, at a concentration between about 0.05% and about 4%.

In one or more embodiments, the NSAID is selected from the group consisting of dicarboxylic acids, having between about 6 and about 14 carbon atoms in their carbon atom skeleton, as well as their salts and derivatives thereof at a concentration between about 1% and about 24%.

In one or more embodiments, the NSAID is a dicarboxylic acid, salts and derivatives thereof at a concentration between about 1% and about 24%.

In one or more embodiments, the NSAID is azelaic acid, salts and derivatives thereof at a concentration between about 1% and about 24%.

In one or more embodiments, the NSAID is an inhibitor of a pro-inflammatory cytokine, at a concentration between about 0.01% and about 10%.

Several disorders of the skin, a body cavity or mucosal surface (e.g., the mucosa of the nose, mouth, eye, ear, vagina or rectum), involve a combination of inflammation and other etiological factors. For example, psoriasis involves inflammation, excessive cell proliferation and inadequate cell differentiation. Atopic dermatitis involves inflammation and skin dryness. Bacterial, fungal and viral infections involve pathogen colonization at the affected site and inflammation. Hence, in many cases, the inclusion of an additional therapeutic agent in the foamable pharmaceutical composition of the present invention, contributes to the clinical activity of the NSAID. Thus, in one or more embodiments, the foamable composition further includes at least one additional therapeutic agent, in a therapeutically effective concentration.

In one or more embodiments, the at least one additional therapeutic agent is selected from the group consisting of an anti-infective, an antibiotic, an antibacterial agent, an antifungal agent, an antiviral agent, an antiparasitic agent, an steroidal antiinflammatory agent, a nonsterolidal anti-inflammatory agent, an immunosuppressive agent, an immunomodulator, an immunoregulating agent, a hormonal agent, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, an anti-wrinkle agent, a radical scavenger, a metal oxide (e.g., titanium dioxide, zinc oxide, zirconium oxide, iron oxide), silicone oxide, an anti wrinkle agent, a skin whitening agent, a skin protective agent, a masking agent, an anti-wart agent, a refatting agent, a lubricating agent and mixtures thereof.

In certain cases, the disorder to be treated involves unaesthetic lesions that need to be masked. For example, rosacea involves papules and pustules, which can be treated with the NSAID, as well as erythema, telangiectasia and redness, which do not respond to treatment with an NSAID. Thus, in one or more embodiments, the additional active agent is a masking agent, i.e., a pigment. Non limiting examples of suitable pigments include brown, yellow or red iron oxide or hydroxides, chromium oxides or hydroxides, titanium oxides or hydroxides, zinc oxide, FD&C Blue No. 1 aluminum lake, FD&C Blue No. 2 aluminum lake and FD&C Yellow No. 6 aluminum lake.

The foamable composition of the present invention can be an emulsion, or microemulsion, including an aqueous phase and an organic carrier phase. The organic carrier is selected from a hydrophobic organic carrier (also termed herein "hydrophobic solvent"), an emollient, a polar solvent, and a mixture thereof.

A "hydrophobic organic carrier" as used herein refers to a material having solubility in distilled water at ambient temperature of less than about 1 gm per 100 mL, more preferable less than about 0.5 gm per 100 mL, and most preferably less than about 0.1 gm per 100 mL. It is liquid at ambient temperature. The identification of a hydrophobic organic carrier or "hydrophobic solvent", as used herein, is not intended to characterize the solubilization capabilities of the solvent for any specific active agent or any other component of the foamable composition. Rather, such information is provided to aid in the identification of materials suitable for use as a hydrophobic carrier in the foamable compositions described herein.

In one or more embodiments, the hydrophobic organic carrier is an oil, such as mineral oil. Mineral oil (Chemical Abstracts Service Registry number 8012-95-1) is a mixture of aliphatic, naphthalenic, and aromatic liquid hydrocarbons that derive from petroleum. It is typically liquid; its viscosity is in the range of between about 35 CST and about 100 CST (at 40° C.), and its pour point (the lowest temperature at which an oil can be handled without excessive amounts of wax crystals forming so preventing flow) is below 0° C. The term hydrophobic organic carrier does not include thick or semi-solid materials, such as white petrolatum, also termed "Vaseline", which, in certain compositions is disadvantageous due to its waxy nature and semi-solid texture.

According to one or more embodiments, hydrophobic solvents are liquid oils originating from vegetable, marine or animal sources. Suitable liquid oil includes saturated, unsaturated or polyunsaturated oils. By way of example, the unsaturated oil may be olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils or mixtures thereof, in any proportion.

Suitable hydrophobic solvents also include polyunsaturated oils containing poly-unsaturated fatty acids. In one or more embodiments, the unsaturated fatty acids are selected from the group of omega-3 and omega-6 fatty acids. Examples of such polyunsaturated fatty acids are linoleic and linolenic acid, gamma-linoleic acid (GLA), eicosapentaenoic acid (EPA) and docosahexaenoic acid (DHA). Such unsaturated fatty acids are known for their skin-conditioning effect, which contribute to the therapeutic benefit of the present foamable composition. Thus, the hydrophobic solvent can include at least 6% of an oil selected from omega-3 oil, omega-6 oil, and mixtures thereof. In the context of the present invention, oils that possess therapeutically-beneficial properties are termed "therapeutically active oil".

Another class of hydrophobic solvents is the essential oils, which are also considered therapeutically active oil, which contain active biologically occurring molecules and, upon topical application, exert a therapeutic effect, which is conceivably synergistic to the beneficial effect of the NSAID in the composition.

Another class of therapeutically active oils includes liquid hydrophobic plant-derived oils, which are known to possess therapeutic benefits when applied topically.

Silicone oils also may be used and are desirable due to their known skin protective and occlusive properties. Suitable silicone oils include non-volatile silicones, such as polyalkyl siloxanes, polyaryl siloxanes, polyalkylaryl siloxanes and polyether siloxane copolymers, polydimethylsiloxanes (dimethicones) and poly(dimethylsiloxane)-(diphenyl-siloxane) copolymers. These are chosen from cyclic or linear polydimethylsiloxanes containing from about 3 to about 9, preferably from about 4 to about 5, silicon atoms. Volatile silicones such as cyclomethicones can also be used. Silicone oils are also considered therapeutically active oil, due to their barrier retaining and protective properties.

In one or more embodiments, the hydrophobic carrier includes at least 2% by weight silicone oil or at least 5% by weight.

The solvent may be a mixture of two or more of the above hydrophobic solvents in any proportion.

A further class of solvents includes "emollients" that have a softening or soothing effect, especially when applied to body areas, such as the skin and mucosal surfaces. Emollients are not necessarily hydrophobic. Examples of suitable emollients include hexyleneglycol, propylene glycol, isostearic acid derivatives, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, sucrose esters of fatty acids, octyl hydroxystearate and mixtures thereof.

According to one or more embodiments of the present invention, the hydrophobic organic carrier includes a mixture of a hydrophobic solvent and an emollient. According to one or more embodiments, the foamable composition is a mixture of mineral oil and an emollient in a ratio between 2:8 and 8:2 on a weight basis.

A "polar solvent" is an organic solvent, typically soluble in both water and oil. Examples of polar solvents include polyols, such as glycerol (glycerin), propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, other glycols, sulfoxides, such as dimethylsulfoxide (DMSO), dimethylformamide, methyl dodecyl sulfoxide, dimethylacetamide, monooleate of ethoxylated glycerides (with 8 to 10 ethylene oxide units), azone (1-dodecylazacycloheptan-2-one), 2-(n-nonyl)-1,3-dioxolane, esters, such as isopropyl myristate/palmitate, ethyl acetate, butyl acetate, methyl proprionate, capric/caprylic triglycerides, octylmyristate, dodecyl-myristate; myristyl alcohol, lauryl alcohol, lauric acid, lauryl lactate ketones; amides, such as acetamide oleates such as triolein; various alkanoic acids such as caprylic acid; lactam compounds, such as azone; alkanols, such as dialkylamino acetates, and admixtures thereof.

According to one or more embodiments, the polar solvent is a polyethylene glycol (PEG) or PEG derivative that is liquid at ambient temperature, including PEG200 (MW (molecular weight) about 190-210 kD), PEG300 (MW about 285-315 kD), PEG400 (MW about 380-420 kD), PEG600 (MW about 570-630 kD) and higher MW PEGs such as PEG 4000, PEG 6000 and PEG 10000 and mixtures thereof.

The polymeric agent serves to stabilize the foam composition and to control drug residence in the target organ. Exemplary polymeric agents, are classified below in a non-limiting manner. In certain cases, a given polymer can belong to more than one of the classes provided below.

In one or more embodiments, the composition of the present invention includes at least one gelling agent. A gelling agent controls the residence of a therapeutic composition in the target site of treatment by increasing the viscosity of the composition, thereby limiting the rate of its clearance from the site. Many gelling agents are known in the art to possess mucoadhesive properties.

The gelling agent can be a natural gelling agent, a synthetic gelling agent and an inorganic gelling agent. Exemplary gelling agents that can be used in accordance with one or more embodiments of the present invention include, for example, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), guar gum, hydroxypropyl guar gum, soluble starch, cationic celluloses, cationic guars, and the like, and synthetic polymeric materials, such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. Mixtures of the above compounds are contemplated.

Further exemplary gelling agents include the acrylic acid/ethyl acrylate copolymers and the carboxyvinyl polymers sold, for example, by the B. F. Goodrich Company under the trademark of Carbopol® resins. These resins consist essentially of a colloidal water-soluble polyalkenyl polyether crosslinked polymer of acrylic acid crosslinked with from 0.75% to 2% of a crosslinking agent such as polyallyl sucrose or polyallyl pentaerythritol. Examples include Carbopol® 934, Carbopol® 940, Carbopol® 950, Carbopol® 980, Carbopol® 951 and Carbopol®) 981. Carbopole 934 is a water-soluble polymer of acrylic acid crosslinked with about 1% of a polyallyl ether of sucrose having an average of about 5.8 allyl groups for each sucrose molecule.

In one or more embodiment, the composition of the present invention includes at least one polymeric agent, which is a water-soluble cellulose ether. Preferably, the water-soluble cellulose ether is selected from the group consisting of methylcellulose, hydroxypropyl cellulose, hydroxypropyl methylcellulose (Methocel), hydroxyethyl cellulose, methylhydroxyethylcellulose, methylhydroxypropylcellulose, hydroxyethylcarboxymethylcellulose, carboxymethylcellulose and carboxymethylhydroxyethylcellulose. More preferably, the water-soluble cellulose ether is selected from the group consisting of methylcellulose, hydroxypropyl cellulose and hydroxypropyl methylcellulose (Methocel). In one or more embodiments, the composition includes a combination of a water-soluble cellulose ether; and a naturally-occurring polymeric materials, selected from the group including xanthan gum, guar gum, carrageenan gum, locust bean gum and tragacanth gum.

Yet, in other embodiments, the gelling agent includes inorganic gelling agents, such as silicone dioxide (fumed silica).

Mucoadhesive/bioadhesion has been defined as the attachment of synthetic or biological macromolecules to a biological tissue. Mucoadhesive agents are a class of polymeric biomaterials that exhibit the basic characteristic of a hydrogel, i.e. swell by absorbing water and interacting by means of adhesion with the mucous that covers epithelia. Compositions of the present invention may contain a mucoadhesive macromolecule or polymer in an amount sufficient to confer bioadhesive properties. The bioadhesive macromolecule enhances the delivery of biologically active agents on or through the target surface. The mucoadhesive macromolecule may be selected from acidic synthetic polymers, preferably having at least one acidic group per four repeating or monomeric subunit moieties, such as poly(acrylic)- and/or poly(methacrylic) acid (e.g., Carbopol®, Carbomer®), poly(methylvinyl ether/maleic anhydride) copolymer, and their mixtures and copolymers; acidic synthetically modified natural polymers, such as carboxymethylcellulose (CMC); neutral synthetically modified natural polymers, such as (hydroxypropyl)methylcellulose; basic amine-bearing polymers such as chitosan; acidic polymers obtainable from natural sources, such as alginic acid, hyaluronic acid, pectin, gum tragacanth, and karaya gum; and neutral synthetic polymers, such as polyvinyl alcohol or their mixtures. An additional group of mucoadhesive polymers includes natural and chemically modified cyclodextrin, especially hydroxypropyl-β-cyclodextrin. Such polymers may be present as free acids, bases, or salts, usually in a final concentration of about 0.01% to about 0.5% by weight.

A suitable bioadhesive macromolecule is the family of acrylic acid polymers and copolymers, (e.g., Carbopol®). These polymers contain the general structure —[$CH_2$—CH (COOH)—]$_n$. Hyaluronic acid and other biologically-derived polymers may be used.

Exemplary bioadhesive or mucoadhesive macromolecules have a molecular weight of at least 50 kDa, or at least 300 kDa, or at least 1,000 kDa. Favored polymeric ionizable macromolecules have not less than 2 mole percent acidic groups (e.g., COOH, $SO_3H$) or basic groups ($NH_2$, NRH, $NR_2$), relative to the number of monomeric units. The acidic or basic groups can constitute at least 5 mole percent, or at least 10 mole percent, or at least 25, at least 50 more percent, or even up to 100 mole percent relative to the number of monomeric units of the macromolecule.

Yet, another group of mucoadhesive agent includes inorganic gelling agents such as silicon dioxide (fumed silica), including but not limited to, AEROSIL 200 (DEGUSSA).

Many mucoadhesive agents are known in the art to also possess gelling properties.

The foam composition may contain a film forming component. The film forming component may include at least one water-insoluble alkyl cellulose or hydroxyalkyl cellulose. Exemplary alkyl cellulose or hydroxyalkyl cellulose polymers include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross linking agent may be used to modify the polymer's characteristics. For example, esters such as dibutyl or diethyl phthalate, amides such as diethyidiphenyl urea, vegetable oils, fatty acids and alcohols such as oleic and myristyl acid may be used in combination with the cellulose derivative.

In one or more embodiments, the composition of the present invention includes a phase change polymer, which alters the composition behavior from fluid-like prior to administration to solid-like upon contact with the target mucosal surface. Such phase change results from external stimuli, such as changes in temperature or pH and exposure to specific ions (e.g., $Ca^{2+}$).

Non-limiting examples of phase change polymers include poly(N-isopropylamide) and Poloxamer 407®.

The polymeric agent is present in an amount in the range of about 0.01% to about 5.0% by weight of the foam composition. In one or more embodiments, it is typically less than about 1 wt % of the foamable composition.

Surface-active agents (also termed "surfactants") include any agent linking oil and water in the composition, in the form of emulsion. A surfactant's hydrophilic/lipophilic balance (HLB) describes the emulsifier's affinity toward water or oil. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average).

According to one or more embodiments of the present invention, the surface-active agent has a hydrophilic lipophilic balance (HLB) between about 9 and about 14, which is the required HLB (the HLB required to stabilize an O/W emulsion of a given oil) of most oils and hydrophobic solvents. Thus, in one or more embodiments, the composition contains a single surface active agent having an HLB value between about 9 and 14, and in one or more embodiments, the composition contains more than one surface active agent and the weighted average of their HLB values is between about 9 and about 14. Yet, in other embodiments, when a water in oil emulsion is desirable, the composition contains one or more surface active agents, having an HLB value between about 2 and about 9.

The surface-active agent is selected from anionic, cationic, nonionic, zwitterionic, amphoteric and ampholytic surfactants, as well as mixtures of these surfactants. Such surfactants are well known to those skilled in the therapeutic and cosmetic formulation art. Nonlimiting examples of possible surfactants include polysorbates, such as polyoxyethylene (20) sorbitan monostearate (Tween 60) and poly (oxyethylene) (20) sorbitan monooleate (Tween 80); poly (oxyethylene) (POE) fatty acid esters, such as Myrj 45, Myrj 49, Myrj 52 and Myrj 59; poly(oxyethylene) alkylyl ethers, such as poly(oxyethylene) cetyl ether, poly(oxyethylene) palmityl ether, polyethylene oxide hexadecyl ether, polyethylene glycol cetyl ether, brij 38, brij 52, brij 56 and brij W1; sucrose esters, partial esters of sorbitol and its anhydrides, such as sorbitan monolaurate and sorbitan monolaurate; mono or diglycerides, isoceteth-20, sodium methyl cocoyl taurate, sodium methyl oleoyl taurate, sodium lauryl sulfate, triethanolamine lauryl sulfate and betaines.

In one or more embodiments of the present invention, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. We have surprisingly found that non-ionic surfactants alone provide foams of excellent quality, i.e. a score of "E" according to the grading scale discussed herein below.

In one or more embodiments, the surface active agent includes a mixture of at least one non-ionic surfactant and at least one ionic surfactant in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1.

In one or more embodiments of the present invention, a combination of a non-ionic surfactant and an ionic surfactant (such as sodium lauryl sulphate and cocamidopropylbetaine) is employed, at a ratio of between 1:1 and 20:1, or at a ratio of 4:1 to 10:1. The resultant foam has a low specific gravity, e.g., less than 0.1 g/ml.

It has been surprisingly discovered that the stability of the composition is especially pronounced when a combination of at least one non-ionic surfactant having HLB of less than 9 and at least one non-ionic surfactant having HLB of equal or more than 9 is employed. The ratio between the at least one non-ionic surfactant having HLB of less than 9 and the at least one non-ionic surfactant having HLB of equal or more than 9, is between 1:8 and 8:1, or at a ratio of 4:1 to 1:4. The resultant HLB of such a blend of at least two emulsifiers is between about 9 and about 14.

Thus, in an exemplary embodiment, a combination of at least one non-ionic surfactant having HLB of less than 9 and at least one non-ionic surfactant having HLB of equal or more than 9 is employed, at a ratio of between 1:8 and 8:1, or at a ratio of 4:1 to 1:4, wherein the HLB of the combination of emulsifiers is between about 9 and about 14.

In one or more embodiments of the present invention, the surface-active agent includes mono-, di- and tri-esters of sucrose with fatty acids (sucrose esters), prepared from sucrose and esters of fatty acids or by extraction from sucro-glycerides. Suitable sucrose esters include those having high monoester content, which have higher HLB values.

The total surface active agent is in the range of about 0.1 to about 5% of the foamable composition, and is typically less than about 2% or less than about 1%.

Preferably, a therapeutically effective foam adjuvant is included in the foamable compositions of the present invention to increase the foaming capacity of surfactants and/or to stabilize the foam. In one or more embodiments of the present invention, the foam adjuvant agent includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains. Foam adjuvants, as defined herein are also useful in facilitating improved spreadability and absorption of the composition.

In one or more embodiments of the present invention, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

In one or more embodiments, a combination of a fatty acid and a fatty ester is employed.

Optionally, the carbon atom chain of the fatty alcohol or the fatty acid may have at least one double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

An important property of the fatty alcohols and fatty acids used in context of the composition of the present invention is related to their therapeutic properties per se. Long chain saturated and mono unsaturated fatty alcohols, e.g., stearyl alcohol, erucyl alcohol, arachidyl alcohol and behenyl alcohol (docosanol) have been reported to possess antiviral, antiinfective, antiproliferative and antiinflammatory properties (see, for example, U.S. Pat. No. 4,874,794). Longer chain fatty alcohols, e.g., tetracosanol, hexacosanol, heptacosanol, octacosanol, triacontanol, etc., are also known for their metabolism modifying properties and tissue energizing properties. Long chain fatty acids have also been reported to possess anti-infective characteristics.

Thus, in preferred embodiments of the present invention, a combined and enhanced therapeutic effect is attained by including both a nonsteroidal immunomodulating agent and a therapeutically effective foam adjuvant in the same composition, thus providing a simultaneous anti-inflammatory and antiinfective effect from both components. Furthermore, in a further preferred embodiment, the composition concurrently comprises a nonsteroidal immunomodulating agent, a therapeutically effective foam adjuvant and a therapeutically active oil, as detailed above. Such combination provides an even more enhanced therapeutic benefit. Thus, the foamable carrier, containing the foam adjuvant provides an extra therapeutic benefit in comparison with currently used vehicles, which are inert and non-active.

The foam adjuvant according to preferred embodiments of the present invention includes a mixture of fatty alcohols, fatty acids and hydroxy fatty acids and derivatives thereof in any proportion, providing that the total amount is 0.1% to 5% (w/w) of the carrier mass. More preferably, the total amount is 0.4%-2.5% (w/w) of the carrier mass.

The therapeutic foam of the present invention may further optionally include a variety of formulation excipients, which are added in order to fine-tune the consistency of the formulation, protect the formulation components from degradation and oxidation and modify their consistency. Such excipients may be selected, for example, from stabilizing agents, antioxidants, humectants, preservatives, colorant and odorant agents and other formulation components, used in the art of formulation.

Aerosol propellants are used to generate and administer the foamable composition as a foam. The total composition including propellant, foamable compositions and optional ingredients is referred to as the foamable carrier. The propellant makes up about 3% to about 25 wt % of the foamable carrier. Examples of suitable propellants include volatile hydrocarbons such as butane, propane, isobutane or mixtures thereof, and fluorocarbon gases.

Composition and Foam Physical Characteristics

A pharmaceutical or cosmetic composition manufactured using the foam carrier according to one or more embodiments of the present invention is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foam composition of the present invention creates a stable emulsion having an acceptable shelf-life of at least one year, or at least two years at ambient temperature. A feature of a product for cosmetic or medical use is long term stability. Propellants, which are a mixture of low molecular weight hydrocarbons, tend to impair the stability of emulsions. It has been observed, however, that emulsion foam compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam. Compositions containing semi-solid hydrophobic solvents, e.g., white petrolatum, as the main ingredients of the oil phase of the emulsion, exhibit high viscosity and poor flowability and are inappropriate candidates for a foamable composition.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administratable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

As further aspect of the foam is breakability. The breakable foam is thermally stable, yet breaks under sheer force. Sheer-force breakability of the foam is clearly advantageous over thermally-induced breakability. Thermally sensitive foams immediately collapse upon exposure to skin temperature and, therefore, cannot be applied on the hand and afterwards delivered to the afflicted area.

Another property of the foam is specific gravity, as measured upon release from the aerosol can. Typically, foams have specific gravity of less than 0.1 g/mL or less than 0.05 g/mL.

Fields of Pharmaceutical Applications

By including an appropriate nonsteroidal immunomodulating agent and optional active agents in the compositions of the present invention, the composition are useful in treating a patient having any one of a variety of dermatological disorders, which include inflammation as one or their etiological factors (also termed "dermatoses"), such as classified in a non-limiting exemplary manner according to the following groups:

Dermatitis including contact dermatitis, atopic dermatitis, seborrheic dermatitis, nummular dermatitis, chronic dermatitis of the hands and feet, generalized exfoliative dermatitis, stasis dermatitis; lichen simplex chronicus; diaper rash;

Bacterial infections including cellulitis, acute lymphangitis, lymphadenitis, erysipelas, cutaneous abscesses, necrotizing subcutaneous infections, staphylococcal scalded skin syndrome, folliculitis, furuncles, hidradenitis suppurativa, carbuncles, paronychial infections, erythrasma;

Fungal Infections including dermatophyte infections, yeast Infections; parasitic Infections including scabies, pediculosis, creeping eruption;

Viral Infections;

Disorders of hair follicles and sebaceous glands including acne, rosacea, perioral dermatitis, hypertrichosis (hirsutism), alopecia, including male pattern baldness, alopecia areata, alopecia universalis and alopecia totalis; pseudofolliculitis barbae, keratinous cyst;

Scaling papular diseases including psoriasis, pityriasis rosea, lichen planus, pityriasis rubra pilaris;

Benign tumors including moles, dysplastic nevi, skin tags, lipomas, angiomas, pyogenic granuloma, seborrheic keratoses, dermatofibroma, keratoacanthoma, keloid;

Malignant tumors including basal cell carcinoma, squamous cell carcinoma, malignant melanoma, paget's disease of the nipples, kaposi's sarcoma;

Reactions to sunlight including sunburn, chronic effects of sunlight, photosensitivity;

Bullous diseases including pemphigus, bullous pemphigoid, dermatitis herpetiformis, linear immunoglobulin A disease;

Pigmentation disorders including hypopigmentation such as vitiligo, albinism and postinflammatory hypopigmentation and hyperpigmentation such as melasma (chloasma), drug-induced hyperpigmentation, postinflammatory hyperpigmentation;

Disorders of cornification including ichthyosis, keratosis pilaris, calluses and corns, actinic keratosis;

Pressure sores;

Disorders of sweating; and

Inflammatory reactions including drug eruptions, toxic epidermal necrolysis; erythema multiforme, erythema nodosum, granuloma annulare.

According to one or more embodiments of the present invention, the compositions are also useful in the therapy of non-dermatological disorders by providing transdermal delivery of an active nonsteroidal immunomodulating agent that is effective against non-dermatological disorders.

The same advantage is expected when the composition is topically applied to a body cavity or mucosal surface (e.g., the mucosa of the nose, mouth, eye, ear, vagina or rectum) to treat conditions such as chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranuloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

The following examples exemplify the therapeutic kits and pharmacological compositions and methods described herein. The examples are for the purposes of illustration only and are not intended to be limiting of the invention.

Example 1—Oil in Water Foamable Compositions (~12% oil) Including Dicarboxylic Acids and Derivatives Thereof

| Ingredient | Composition No: | | | |
|---|---|---|---|---|
| | AZ-1 | DA-2 | DA-3 | DA-4 |
| | % | | | |
| Azelaic acid | 15.00 | | | |
| Dimethyl azelate | | 10.00 | | |
| Di(ethyl salicylate) azelate (TU-2100) | | | 10.00 | |
| Sebacic acid | | | | 10.00 |
| Mineral oil | 5.60 | 5.60 | 5.60 | 5.60 |
| Isopropyl palmitate | 5.60 | 5.60 | 5.60 | 5.60 |
| Sorbitan stearate (Span 60) | 2.00 | 2.00 | 2.00 | 2.00 |
| PPG15-stearyl ether | 1.00 | 1.00 | 1.00 | 1.00 |
| Stearic acid | 0.85 | 0.85 | 0.85 | 0.85 |
| Glyceryl monostearate | 0.45 | 0.45 | 0.45 | 0.45 |
| Xanthan gum | 0.26 | 0.26 | 0.26 | 0.26 |
| Methocel K100M | 0.26 | 0.26 | 0 | 0 |
| Preservative | 0.25 | 0.25 | 0.25 | 0.25 |
| Propellant | 10.00 | 10.00 | 10.00 | 10.00 |
| Water | To 100 | To 100 | To 100 | To 100 |

Example 2—Oil in Water Foamable Compositions (~30% oil) Including Dicarboxylic Acids and Derivatives Thereof

| Ingredient | Composition No: | | | |
|---|---|---|---|---|
| | AZ-2 | DA-5 | DA-6 | DA-7 |
| | % | | | |
| Azelaic acid | 15.00 | | | |
| Dimethyl azelate | | 5.00 | | |
| Di(ethyl salicylate) azelate (TU-2100) | | | 10.00 | |
| Sebacic acid | | | | 10.00 |
| MCT oil | 30.00 | 30.00 | 30.00 | 30.00 |
| Glyceryl monostearate | 0.50 | 0.50 | 0.50 | 0.50 |
| Stearyl alcohol | 1.00 | 1.00 | 1.00 | 1.00 |
| Xanthan gum | 0.30 | 0.30 | 0.30 | 0.30 |
| Methocel K100M | 0.30 | 0.30 | 0.30 | 0.30 |
| Polysorbate 80 | 1.00 | 1.00 | 1.00 | 1.00 |
| PEG-40 stearate | 3.00 | 3.00 | 3.00 | 3.00 |
| Cocamidopropyl betaine | 0.50 | 0.50 | 0.50 | 0.50 |
| Preservative | 0.25 | 0.25 | 0.25 | 0.25 |
| Propellant | 16.00 | 16.00 | 16.00 | 16.00 |
| Water | To 100 | To 100 | To 100 | To 100 |

Example 3—COX Inhibitor Oil in Water Foamable Compositions

| Ingredient | Composition No: | | | | |
|---|---|---|---|---|---|
| | CX-1 | CX-2 | CX-3 | CX-4 | CX-5 |
| | % | | | | |
| Ethyl salicylate | 4.00 | | | | |
| Diclofenac | | 1.00 | 3.00 | | |
| Salicylic acid | | | | 2.00 | 5.00 |
| Mineral oil | 5.60 | 5.60 | 5.60 | 5.60 | 5.60 |
| Capric caprylic triglyceride | 5.60 | 5.60 | 5.60 | 5.60 | 5.60 |
| PEG-40 stearate | 2.80 | 2.80 | 2.80 | 2.80 | 2.80 |
| Propylene glycol | — | 2.00 | — | — | — |
| Polysorbate 80 | 0.90 | 0.90 | 0.90 | 0.90 | 0.90 |
| Stearic acid | 0.90 | 0.90 | 0.90 | 0.90 | 0.90 |
| Glyceryl monostearate | 0.45 | 0.45 | 0.45 | 0.45 | 0.45 |
| Xanthan gum | 0.28 | 0.28 | 0.28 | 0.28 | 0.28 |
| Methocel K100M | 0.28 | 0.28 | 0.28 | — | — |
| Preservative | 0.25 | 0.25 | 0.25 | 0.25 | 0.25 |
| Propellant | 8.00 | 8.00 | 8.00 | 8.00 | 8.00 |
| Water | To 100 | To 100 | To 100 | To 100 | To 100 |

Example 4—Ketoconazole Oil in Water Compositions

| Ingredient | Composition Code: | | | | | |
|---|---|---|---|---|---|---|
| | KF-1 | KF-2 | KF-3 | KF-4 | KF-5 | KF-6 |
| | % | | | | | |
| Ketoconazole | 0.01 | 0.10 | 0.20 | 0.30 | 0.50 | 1.00 |
| Water | 72.82 | 71.83 | 71.73 | 72.53 | 72.33 | 71.83 |
| Mineral oil | 14.10 | 15.00 | 15.00 | 14.10 | 14.10 | 14.10 |
| Span 60 | 2.00 | 2.00 | 2.00 | 2.00 | 2.00 | 2.00 |
| PPG15-stearyl ether | 1.00 | 1.00 | 1.00 | 1.00 | 1.00 | 1.00 |
| Stearic acid | 0.85 | 0.85 | 0.85 | 0.85 | 0.85 | 0.85 |
| Glyceryl monostearate | 0.45 | 0.45 | 0.45 | 0.45 | 0.45 | 0.45 |
| Xanthan gum | 0.26 | 0.26 | 0.26 | 0.26 | 0.26 | 0.26 |
| Methocel K100M | 0.26 | 0.26 | 0.26 | 0.26 | 0.26 | 0.26 |
| Phenochem | 0.25 | 0.25 | 0.25 | 0.25 | 0.25 | 0.25 |
| Propellant | 8.00 | 8.00 | 8.00 | 8.00 | 8.00 | 8.00 |
| Water | 100 | 100 | 100 | 100 | 100 | 100 |
| Composition Properties | | | | | | |
| Emulsion color | White | White | White | White | White | White |
| Foam Density | 0.06 | 0.23 | 0.33 | 0.12 | 0.16 | 0.16 |

Example 5—Water in Oil Diclofenac Sodium Compositions

| Ingredient | Composition Code: | | | |
|---|---|---|---|---|
| | DC3 | DC4 | DC5 | D3IC3 |
| | % | | | |
| Diclofenac sodium (active agent) | 1.00 | 1.00 | 1.00 | 3.00 |
| Transcutol P (Penetration enhancer) | 8.00 | | | |
| Propylene glycol (Penetration enhancer) | | 3.00 | | |
| Mineral oil | 5.60 | 5.60 | 5.60 | 5.60 |
| Isopropyl myristate | 5.60 | 5.60 | 5.60 | 5.60 |
| Glyceryl monostearate | | | | 0.45 |
| Stearyl alcohol | 0.85 | 0.85 | 0.85 | 0.85 |
| Xanthan gum | 0.25 | 0.25 | 0.25 | 0.26 |
| Hydroxypropyl methylcellulose | 0.25 | 0.25 | 0.25 | |
| Polysorbate 80 | 0.85 | 0.85 | 0.85 | |
| Polysorbate 60 | | | | 0.90 |
| PEG-40 stearate | 2.50 | 2.50 | 2.50 | 2.60 |
| Polyoxyethylene (2) Stearyl Ether | | | | 3.00 |
| Polyoxyethylene (21) Stearyl Ether | | | | 2.00 |
| Cocoamidopropylbethaine | 0.40 | 0.40 | 0.40 | |
| Preservative | 0.30 | 0.30 | 0.30 | |
| Propellant | 8.00 | 8.00 | 8.00 | 8.00 |
| Purified water | To 100 | To 100 | To 100 | To 100 |
| Composition Properties | | | | |
| Foam Quality | E | E | E | E |
| Density | 0.028 | 0.033 | 0.030 | 0.043 |

Example 6—Stability of Composition D3IC3

Following the preparation of Composition D3IC3, it was tested for physical stability, ane the results were as follows:

| Test | Baseline | End of Program |
|---|---|---|
| 4 Freeze-Thaw cycles (−10°/+40°) - Foam Quality | Excellent | Excellent |
| 4 Freeze-Thaw cycles (−10°/+40°) - Density | 0.043 | 0.045 |
| Centrifugation (10,000 rpm, 10 min) | No separation | No separation |
| 3 months at 25° C. - Foam Quality | Excellent | Excellent |
| 3 months at 25° C. - Phase separation | None | None |
| 3 months at 25° C. - Density | 0.043 | 0.040 |
| 3 months at 25° C. - Color | White | White |
| 3 months at 25° C. - Odor | Very faint typical | Very faint typical |
| 3 months at 40° C. - Foam Quality | Excellent | Excellent |
| 3 months at 40° C. - Phase separation | None | None |
| 3 months at 40° C. - Density | 0.043 | 0.038 |
| 3 months at 40° C. - Color | White | White |
| 3 months at 40° C. - Odor | Very faint typical | Very faint typical |

These results indicate that the foamable formulation of the present invention is physically stable.

Example 7—Water in Oil Nonsteroidal Immunomodulating Compositions

| Ingredient | Composition Code: | | | | | |
|---|---|---|---|---|---|---|
| | WO-1 | WO-2 | WO-3 | WO-4 | WO-5 | WO-6 |
| | % | | | | | |
| Etodolac (active agent) | 1.00 | | | | | |
| Tacrolimus (active agent) | | 2.00 | | | | |
| Ketoconazole (active agent) | | | 2.00 | | | |
| Salicylic acid (active agent) | | | | 5.00 | | |
| Azelaic acid (active agent) | | | | | 15.00 | |
| Thalidomide (active agent) | | | | | | 4.00 |
| Clindamycin (additional active agent) | | | | 2.00 | 2.00 | |
| Mineral oil | 12.00 | 12.00 | 12.00 | 12.00 | 12.00 | 10.00 |
| Isopropyl myristate | 12.00 | 12.00 | 12.00 | 12.00 | 12.00 | 10.00 |
| Dimeticone V100 | 3.00 | 3.00 | 3.00 | 3.00 | 3.00 | |
| Glyceryl monostearate | 0.50 | 0.50 | 0.50 | 0.50 | 0.50 | 0.50 |
| Zinc oxide | 10.00 | 15.00 | 15.00 | 20.00 | 25.00 | |
| Titanium Dioxide | | | | | | 20.00 |
| Alpha-Bisabolol | 0.20 | 0.20 | 0.20 | 0.20 | 0.20 | |
| MYRJ 52 | 3.00 | 3.00 | 3.00 | 3.00 | 3.00 | 3.00 |

-continued

| Ingredient | WO-1 | WO-2 | WO-3 | WO-4 | WO-5 | WO-6 |
|---|---|---|---|---|---|---|
| | \multicolumn{6}{c}{Composition Code: %} | | | | | |
| Microcrystalline cellulose + carboxymethyl cellulose) | 2.00 | 1.00 | 2.00 | 2.00 | 2.00 | 2.00 |
| TWEEN 80 | 1.00 | 1.00 | 1.00 | 1.00 | 1.00 | 1.00 |
| Cocoamidopropylbethaine | 0.50 | 0.50 | 0.50 | 0.50 | 0.50 | 0.50 |
| D-Panthenol 50P | 10.00 | 10.00 | 10.00 | 10.00 | 10.00 | |
| Preservative | 0.30 | 0.30 | 0.30 | 0.30 | 0.30 | 0.30 |
| Purified water | To 100 | To 100 | To 100 | To 100 | To 100 | To 100 |

Example 8—Comparative Study, to Assess the Organoleptic Properties of Foamable Composition According to the Present Invention, vs. Foams According to PCT/AU99/00735

Usability of a pharmaceutical composition and its ease of use is a primary determinant in high treatment compliance and, subsequently, favorable therapeutic results. The present study was performed in order to assess the organoleptic properties of foamable compositions according to the present invention, vs. foams according to PCT/AU99/00735 ('735).

The vehicles of Composition AZ-1 (oil in water emulsion; ~12% oil) according the Examples 1 hereinabove were compared with Composition No. 1 according to the example of PCT/AU99/00735 (oil in water emulsion; 10% oil), in a consumer test panel of six subjects. The panelists were asked to assess the following parameters: appearance, physical disintegration, fluidity, ease of spreading (spreadability), absorbency, residual feeling and oily feeling. As presented in the following table, the majority of panelists determined that the AZ-1 foam was better than Composition No. 1 according to the example of the '735 patent.

| | AZ-1 Better than '735 | '735 Better than AZ-1 | AZ-1 Equals '735 |
|---|---|---|---|
| Appearance | 5 | 0 | 0 |
| Physical disintegration | 5 | 0 | 0 |
| Fluidity | 5 | 0 | 0 |
| Easy to spread | 2 | 0 | 3 |
| Absorbency | 3 | 0 | 2 |
| Residual feeling | 5 | 0 | 0 |
| Oily feeling | 5 | 0 | 0 |

The multiple advantageous features of compositions AZ-1 are presumably attained due to (1) the presence of a foam adjuvant in AZ-1, which contributes to facile spreading and absorbency; and (2) absence of petrolatum in AZ-1, which avoids the residual and oily feeling, typical to petrolatum-containing products.

What is claimed is:

1. A therapeutic kit comprising an aerosol packaging assembly comprising:
   a) a container accommodating a pressurized product; and
   b) an outlet capable of releasing the pressurized product as a foam; wherein the pressurized product comprises:
   (A) a foamable emulsion composition comprising:
      i. a nonsteroidal immunomodulating agent;
      ii. at least one liquid hydrophobic carrier at a concentration of about 20% to about 50% by weight;
      iii. about 0.1% to about 5% by weight of surface active agent;
      iv. about 0.01% to about 5% by weight of at least one polymeric agent selected from the group consisting of a bioadhesive agent, a gelling agent, a film forming agent and a phase change agent; and
      v. water; and
   (B) a liquefied or compressed gas propellant at a concentration of about 3% to about 25% by weight;
   wherein the pressurized product includes less than 5% or about 5% by weight of ethanol, propanol, isopropanol, butanol, iso-butanol, t-butanol, and pentanol, or mixtures of two or more thereof;
   wherein the surface active agent comprises a non-ionic surface active agent and optionally an ionic surface active agent at a maximum amount of less than about 0.72% by weight;
   wherein if ionic surfactant is present the ratio of non-ionic to ionic surface active agent is about 6:1 or greater than 6:1;
   wherein the nonsteroidal immunomodulating agent is substantially or completely dissolved in the oil phase of the emulsion; and
   wherein the pressurized product is released from the container as an expanded, breakable foam that collapses upon application of shear force.

2. A therapeutic foamable composition comprising:
   (a) an emulsion composition comprising:
   i. a nonsteroidal immunomodulating agent;
   ii. about 20% to about 50% by weight of a therapeutically active oil;
   iii. about 0.1% to about 5% by weight of surface active agent;
   iv. about 0.01% to about 5% by weight of at least one polymeric agent selected from the group consisting of a bioadhesive agent, a gelling agent, a film forming agent and a phase change agent; and
   v. water; and
   (b) a liquefied or compressed gas propellant at a concentration of about 3% to about 25% by weight;
   wherein the foamable composition includes less than 5% or about 5% by weight of ethanol, propanol, isopropanol, butanol, iso-butanol, t-butanol and pentanol or mixtures thereof;
   wherein the surface active agent comprises non-ionic surface active agent and optionally ionic surface active agent at a maximum amount of less than about 0.72% by weight;
   wherein if ionic surfactant is present the ratio of non-ionic to ionic surface active agent is about 6:1 or greater than 6:1;

wherein the nonsteroidal immunomodulating agent is substantially or completely dissolved in the oil phase of the emulsion; and wherein upon release from a pressurized canister the foamable composition forms an expanded, breakable foam that collapses upon application of shear force.

3. The kit of claim 1, wherein the polymeric agent is a gelling agent and wherein the propellant is selected from the group consisting of a hydrocarbon, a fluorocarbon, and mixtures thereof.

4. The kit of claim 2, wherein the polymeric agent is a gelling agent and wherein the propellant is selected from the group consisting of a hydrocarbon, a fluorocarbon, or mixtures thereof.

5. The kit of claim 3, wherein the foamable composition is selected from the group consisting of an oil-in-water emulsion and a water-in-oil emulsion.

6. The kit of claim 5, wherein the outlet comprises a valve.

7. The kit of claim 6, wherein the valve comprises a stem with 1 to 4 apertures formed in the stem.

8. The kit of claim 7, wherein each aperture formed in the stem has a diameter selected from the group consisting of (i) about 0.2 mm to about 1 mm; and (ii) about 0.3 mm to about 0.8 mm.

9. The kit of claim 7, wherein the sum of areas of all apertures in the stem is selected from the group consisting of (i) between about 0.01 mm$^2$ and 1 mm$^2$; and (ii) between about 0.04 mm$^2$ and 0.5 mm$^2$.

10. The kit of claim 5, further comprising about 0.1% to about 5% by weight of a therapeutically active foam adjuvant selected from the group consisting of a fatty alcohol having 15 or more carbons in its carbon chain; a fatty acid having 16 or more carbons in its carbon chain; fatty alcohols, derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid; a fatty acid substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid; and mixtures of two or more thereof.

11. The kit of claim 10, wherein the pressurized product includes less than 2% or about 2% by weight of ethanol, propanol, isopropanol, butanol, iso-butanol, t-butanol and pentanol, or mixtures of two or more thereof.

12. The kit of claim 4, wherein the nonsteroidal immunomodulating agent is selected from the group consisting of:
   i. an indole, an indende acetic acid, a heteraryl acetic acid, an arylpropionic acid, an anthranilic acids, a fenamate, an enolic acid, a pyrazolidinedione, and an alkanone; and salts thereof;
   ii. salicylic acid, aspirin, sodium salicylate, choline magnesium trisalicylate, salsalate, diflunisal, salicylsalicylic acid, sulfasalazine, olsalazine, esters of salicylic acid with a carboxylic acid, esters of salicylic acid with a dicarboxylic acid, esters of salicylic acid with a fatty acid, esters of salicylic acid with a hydroxyl fatty acid, esters of salicylic acid with an essential fatty acid, esters of salicylic acid with a polycarboxylic acid, para-aminophenol, indole, indomethacin, sulindac, etodolac, tolmetin, diclofenac, ketorolac, ibuprofen, naproxen, flubiprofen, ketoprofen, fenoprofen, oxaprozin, mefenamic acid, meclofenamic acid, oxicams, piroxicam, tenoxicam, pyrazolidinediones, phenylbutazone, oxyphenthratrazone, nabumetone, diaryl-substituted furanones, Rofecoxib, diaryl-substituted pyrazoles, Celecoxib, indole acetic acids, Etodolac, sulfonanilides, Nimesulide, and salts and analogs thereof;
   iii. an imidazole or triazole compound;
   iv. ketoconazole;
   v. a xanthine, pentoxifylline, propentofylline, torbafylline, amiloride, chloroquine, thalidomide, and salts and analogs thereof;
   vi. a cyclic peptide, cyclosporine, tacrolimus, tresperimus, pimecrolimus, sirolimus, verolimus, laflunimus, laquinimod, and imiquimod;
   vii. a dicarboxylic acid having between about 6 and about 14 carbon atoms in its carbon atom skeleton, and salts thereof;
   viii. adipic acid, pimelic acid, suberic acid, azelaic acid, sebacic acid, 1,11-undecanedioic acid, 1,12-dodecanedioic acid, 1,13-tridecanedioic acid, and 1,14-tetradecanedioic acid;
   ix. azelaic acid; and
   x. a dicarboxylic acid covalently linked with at least one moiety selected from the group consisting of alpha-hydroxy acid, beta-hydroxy acid, hydroxybenzoic acid, alkylhydroxybenzoate, dihydroxy benzene, cresol, alcohol derivatives of Vitamin A, retinoic acid, retinal, steroid hormones, corticosteroids, vitamin E, and vitamin D, and analogs thereof.

13. The kit of claim 10, wherein the concentration range of the nonsteroidal immunomodulating agent is selected from the group consisting of (i) between about 0.05% and about 2% by weight; (ii) between about 2% and about 5% by weight; (iii) between about 5% and about 12% by weight; and (iv) between about 12% and about 24% by weight.

14. The kit of claim 5, wherein the foamable composition further comprises at least one additional therapeutic agent selected from the group consisting of an anti-infective, an antibiotic, an antibacterial agent, an antifungal agent, an antiviral agent, an antiparasitic agent, a steroidal antiinflammatory agent, an immunosuppressive agent, an immunomodulator, an immunoregulating agent, a hormonal agent, a vitamin A, a vitamin B, a vitamin C, a vitamin D, a vitamin E, a vitamin F, a vitamin K, a wound healing agent, a disinfectant, an anesthetic, an antiallergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, benzoyl chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, talc, carbon, an anti wrinkle agent, a skin whitening agent, a skin protective agent, a masking agent, an anti-wart agent, a refatting agent, a lubricating agent, and mixtures of two or more thereof.

15. The kit of claim 3, wherein the concentration of the surface active agent is between about 0.2% and about 2% by weight.

16. The kit of claim 11, wherein the surface active agent includes a mixture of at least one non-ionic surfactant and at least one ionic surfactant in a ratio in the range of about 100:1 to 6:1.

17. The kit of claim 3, wherein the surface active agent is non-ionic.

18. The kit of claim 5, wherein the emulsion is a water-in-oil emulsion.

19. The kit of claim 5, wherein the emulsion is an oil-in-water emulsion.

20. The kit of claim 5, wherein the surface active agent comprises a combination of at least one non-ionic surfactant having a hydrophilic/lipophilic balance (HLB) of less than 9 and at least one non-ionic surfactant having HLB of equal or more than 9, wherein the ratio between the at least one non-ionic surfactant having HLB of less than 9 and the at least one non-ionic surfactant having HLB of equal or more than 9, is between 1:8 and 8:1.

21. The kit of claim 10, wherein the polymeric agent is selected from the group consisting of a water-soluble cellulose ether and a naturally-occurring polymeric material.

22. The kit of claim 10, wherein the polymeric agent is selected from the group consisting of methylcellulose, hydroxypropyl cellulose, hydroxypropyl methylcellulose, hydroxyethyl cellulose, methylhydroxyethylcellulose, methylhydroxypropylcellulose, hydroxyethylcarboxymethylcellulose, carboxymethylcellulose, carboxymethylhydroxyethylcellulose, xanthan gum, guar gum, carrageenin gum, locust bean gum, tragacanth gum, and mixtures of any two or more thereof.

23. The foamable composition of claim 4, further comprising about 0.1% to about 5% by weight of a therapeutically active foam adjuvant selected from the group consisting of a fatty alcohol having 15 or more carbons in their carbon chain; a fatty acid having 16 or more carbons in their carbon chain; fatty alcohols, derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid; a fatty acid substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid; and mixtures of two or more thereof.

24. The foamable composition of claim 23, wherein the foamable composition further comprises at least one additional therapeutic agent.

25. The foamable composition of claim 24, wherein the additional therapeutic agent is selected from the group consisting of an anti-infective, an antibiotic, an antibacterial agent, an antifungal agent, an antiviral agent, an antiparasitic agent, an steroidal antiinflammatory agent, an immunosuppressive agent, an immunomodulator, an immunoregulating agent, a hormonal agent, a vitamin A, a vitamin B, a vitamin C, a vitamin D, a vitamin E, a vitamin F, a vitamin K, a wound healing agent, a disinfectant, an anesthetic, an anti-allergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, benzoyl chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, talc, carbon, an anti wrinkle agent, a skin whitening agent, a skin protective agent, a masking agent, an anti-wart agent, a refatting agent, a lubricating agent, and mixtures of two or more thereof.

26. The kit of claim 10, further comprising at least one organic carrier selected from the group consisting of a polar solvent, an emollient, and mixtures of two or more thereof.

27. The kit of claim 26, wherein the polar solvent comprises propylene glycol.

28. The kit of claim 26, wherein the polar solvent comprises a polyethylene glycol.

29. The kit of claim 10, wherein the foamable composition comprises the ionic surface active agent and the ratio of non-ionic to ionic surface active agent is about 8:1 or greater than 8:1.

30. The kit of claim 11, wherein the foamable composition comprises an ionic surface active agent and the ratio of non-ionic to ionic surface active agent is greater than 16:1.

31. The kit of claim 5, wherein the ratio of non-ionic to ionic surface active agent is about 14:1 or greater than 14:1.

32. The foamable composition of claim 2, wherein the foamable composition comprises the ionic surface active agent and the ratio of non-ionic to ionic surface active agent is about 16:1 or greater than about 16:1.

33. The foamable composition of claim 24, wherein foamable composition comprises the ionic surface active agent and the ratio of non-ionic to ionic surface active agent is about 20:1 or greater than about 20:1.

34. The foamable composition of claim 4, wherein the therapeutically active oil is selected from the group consisting of a polyunsaturated oil, a polyunsaturated fatty acid, an omega-3 fatty acid, an omega-6 fatty acid, linoleic acid, linolenic acid, gamma-linoleic acid (GLA), eicosapentaenoic acid (EPA), docosahexaenoic acid (DHA), an essential oil containing an active biologically occurring molecule, a liquid hydrophobic plant-derived oil possessing therapeutic benefits, and mixtures of any two or more thereof.

35. The kit of claim 3, wherein the nonsteroidal immunomodulating agent is selected from the group consisting of salsalate, salicylsalicylic acid, sulindac, fenoprofen, oxaprozin, meclofenamic acid sirolimus, everolimus, and mixtures of any two or more thereof.

36. The kit of claim 4, wherein the nonsteroidal immunomodulating agent is selected from the group consisting of an indende acetic acid, a heteraryl acetic acid, an arylpropionic acid, an anthranilic acids, olsalazine, tolmetin, oxyphenthratrazone, Rofecoxib, indole acetic acid, nimesulide, a xanthine, pentoxifylline, propentofylline, torbafylline, amiloride, chloroquine, tresperimus, pimecrolimus, laflunimus, laquinimod, and mixtures of any two or more thereof.

* * * * *